US010671969B2

(12) United States Patent
Sayles et al.

(10) Patent No.: US 10,671,969 B2
(45) **Date of Patent: *Jun. 2, 2020**

(54) OPERATING ROOM SITUATED, PARTS-INVENTORY CONTROL SYSTEM AND SUPERVISORY ARRANGEMENT FOR ACCURATELY TRACKING THE USE OF AND ACCOUNTING FOR THE ULTIMATE DISPOSITION OF AN INDIVIDUAL COMPONENT PART OF A COMPLETE IMPLANT WHICH IS THEN BEING SURGICALLY ENGRAFTED IN-VIVO UPON OR INTO THE BODY OF A LIVING SUBJECT

(71) Applicant: Summate Technologies, Inc., Newburyport, MA (US)

(72) Inventors: Philip W. Sayles, Newburyport, MA (US); Todd Rosseau, Newburyport, MA (US)

(73) Assignee: Summate Technologies, Inc., Newburyport, MA (US)

( * ) Notice: Subject to any disclaimer, the term of this patent is extended or adjusted under 35 U.S.C. 154(b) by 190 days.

This patent is subject to a terminal disclaimer.

(21) Appl. No.: 15/731,214

(22) Filed: May 3, 2017

(65) Prior Publication Data

US 2018/0322445 A1 Nov. 8, 2018

(51) Int. Cl.

*A61B 90/90* (2016.01)
*G06Q 10/08* (2012.01)

(Continued)

(52) U.S. Cl.

CPC ..... *G06Q 10/087* (2013.01); *G06K 19/06009* (2013.01); *G16H 20/40* (2018.01); *G16H 40/20* (2018.01)

(58) Field of Classification Search

CPC ...... G06Q 10/087; G16H 20/40; G16H 40/20; G06K 19/06009

(Continued)

(56) References Cited

U.S. PATENT DOCUMENTS

| | | | |
|---|---|---|---|
| 3,967,202 | A | 6/1976 | Batz |
| 4,614,945 | A | 9/1986 | Brunius |

(Continued)

FOREIGN PATENT DOCUMENTS

| | | |
|---|---|---|
| KR | 100875690 | 8/2007 |
| KR | 20070078826 | 8/2007 |

(Continued)

OTHER PUBLICATIONS

Telemetry Group "Telemetry Standard RCC Document 106-07," Chapter 2, Sep. 2007.

(Continued)

*Primary Examiner* — Luna Champagne
(74) *Attorney, Agent, or Firm* — Blueshift IP, LLC; Robert Plotkin

(57) ABSTRACT

The preset invention is an inventory-parts control system and supervisory arrangement suitable for tracking the actual use of and accounting for the ultimate disposition of at least some of the individual pieces constituting an implant (or a complete implant construct), which is then being surgically engrafted in-vivo. This inventory-parts control system and supervisory arrangement is accurate, reliable, and fully functional for inventory part control purposes during the surgery; and will account for the ultimate disposition of each required component item of that implant (or complete implant construct) individually and in a timely manner, as each part is individually surgically introduced and engrafted in-vivo at a preselected anatomic site upon or within the body of a living subject.

5 Claims, 15 Drawing Sheets

Table A: Exemplary Types of Implants (Particularly Prostheses)

ABSORBABLE IMPLANTS
ARTIFICIAL LIMBS
AUDITORY BRAIN STEM IMPLANTS
BIOPROSTHESIS
BLOOD VESSEL PROSTHESIS
BONE-IMPLANT INTERFACE
BREAST IMPLANTS
COCHLEAR IMPLANTS
DENTAL IMPLANTS
    DENTAL IMPLANTS, SINGLE-TOOTH
DENTAL PROSTHESIS
    CROWNS +
    DENTAL ABUTMENTS
    DENTAL CLASPS
    DENTAL PROSTHESIS, IMPLANT-SUPPORTED
    DENTAL RESTORATION, PERMANENT +
    DENTAL RESTORATION, TEMPORARY
    DENTAL VENEERS
    DENTURES +
    PALATAL OBTURATORS
    PERIODONTAL PROSTHESIS
    TOOTH, ARTIFICIAL
ELECTRODES, IMPLANTED
    DEFIBRILLATORS, IMPLANTABLE
    IMPLANTABLE NEUROSTIMULATORS +
EMBOLIC PROTECTION DEVICES
    VENA CAVA FILTERS
EYE, ARTIFICIAL
FIDUCIAL MARKERS
GLAUCOMA DRAINAGE IMPLANTS
    MOLTENO IMPLANTS
HEART VALVE PROSTHESIS
HEART ARTIFICIAL
    HEART-ASSIST DEVICES
IMPLANTS, EXPERIMENTAL
INTERNAL FIXATORS
    BONE NAILS
    BONE PLATES
    BONE SCREWS +
    BONE WIRES
    SUTURE ANCHORS
JOINT PROSTHESIS
    ELBOW PROSTHESIS
    HIP PROSTHESIS
    KNEE PROSTHESIS
    METAL-ON-METAL JOINT PROSTHESES ESES
    SHOULDER PROSTHESIS
LARYNX, ARTIFICIAL
LENSES, INTRAOCULAR
MAXILLOFACIAL PROSTHESIS
    MANDIBULAR PROSTHESIS
ORBITAL IMPLANTS
OSSICULAR PROSTHESIS
PENILE PROSTHESIS
PROSTHESIS DESIGN
    PROSTHESIS COLORING
PUNCTAL PLUGS
SEPTAL OCCLUDER DEVICE
STENTS
    DRUG-ELUTING STENTS
    SELF EXPANDABLE METALLIC STENTS ENTS
SUBURETHRAL SLINGS
TISSUE EXPANSION DEVICES
TISSUE SCAFFOLDS
URINARY SPHINCTER, ARTIFICIAL

(51) Int. Cl.
*G06K 19/06* (2006.01)
*G16H 40/20* (2018.01)
*G16H 20/40* (2018.01)

(58) Field of Classification Search
USPC ........................................................ 705/28
See application file for complete search history.

(56) References Cited

U.S. PATENT DOCUMENTS

| | | | |
|---|---|---|---|
| 4,816,839 | A | 3/1989 | Landt |
| 5,234,433 | A | 8/1993 | Bert |
| 5,528,222 | A | 6/1996 | Moskowitz |
| 5,641,634 | A | 6/1997 | Mandecki |
| 5,682,143 | A | 10/1997 | Brady |
| 5,786,626 | A | 7/1998 | Brady |
| 5,825,298 | A | 10/1998 | Walter |
| 5,874,902 | A | 2/1999 | Heinrich |
| 5,892,458 | A | 4/1999 | Anderer |
| 5,974,078 | A | 10/1999 | Tuttle |
| 6,104,281 | A | 8/2000 | Heinrich |
| 6,147,662 | A | 11/2000 | Grabau |
| 6,177,859 | B1 | 1/2001 | Tuttle |
| 6,293,684 | B1 | 9/2001 | Riblett |
| 6,590,150 | B1 | 7/2003 | Kiefer |
| 6,925,447 | B2 | 8/2005 | McMenimen |
| 7,053,294 | B2 | 5/2006 | Tuttle |
| 7,098,394 | B2 | 8/2006 | Armer |
| 7,135,977 | B2 | 11/2006 | Burg |
| 7,195,149 | B2 | 3/2007 | Baker |
| 7,328,837 | B2 | 2/2008 | Baker |
| 7,412,898 | B1 | 8/2008 | Smith |
| 7,585,302 | B2 | 9/2009 | Revie |
| 7,633,111 | B2 | 12/2009 | Friedrich |
| 7,698,156 | B2 | 4/2010 | Martucci |
| 7,791,481 | B2 | 9/2010 | Landt |
| 7,849,807 | B2 | 12/2010 | Suzuki |
| 7,915,517 | B2 | 3/2011 | Lau |
| 8,027,632 | B2 | 9/2011 | Mazar |
| 8,089,285 | B2 | 1/2012 | Hsu |
| 8,165,658 | B2 | 4/2012 | Waynik |
| 8,350,704 | B2 | 1/2013 | Mullis |
| 8,353,917 | B2 | 1/2013 | Mandecki |
| 8,476,689 | B2 | 7/2013 | Chang |
| 8,501,122 | B2 | 8/2013 | Shirazi |
| 8,540,468 | B2 | 9/2013 | Mekid |
| 8,552,470 | B2 | 10/2013 | Chen |
| 8,574,946 | B1 | 11/2013 | Martin |
| 8,576,050 | B2 | 11/2013 | Hansen |
| 8,587,406 | B2 | 11/2013 | Maltseff |
| 8,587,410 | B2 | 11/2013 | Potyrailo |
| 8,596,544 | B2 | 12/2013 | Kang |
| 8,616,459 | B2 | 12/2013 | Sykkoe |
| 8,624,294 | B2 | 1/2014 | Kline |
| 8,628,018 | B2 | 1/2014 | Zenz |
| 8,636,220 | B2 | 1/2014 | Warther |
| 8,660,640 | B2 | 2/2014 | Markowitz |
| 8,663,120 | B2 | 3/2014 | Markowitz |
| 8,717,430 | B2 | 5/2014 | Simon |
| 8,796,186 | B2 | 8/2014 | Shirazi |
| 8,996,393 | B2 | 3/2015 | Sobie |
| 9,313,558 | B1 | 4/2016 | Mandecki |
| 9,361,568 | B2 | 6/2016 | Butler |
| 9,370,401 | B2 | 6/2016 | Sayles |
| 9,405,950 | B2 | 8/2016 | Mats |
| 9,418,263 | B2 | 8/2016 | Butler |
| 9,418,321 | B1 | 8/2016 | Gruda |
| 9,847,044 | B1 | 12/2017 | Foster |
| 9,964,134 | B1 | 5/2018 | Tran |
| 10,470,809 | B1 | 11/2019 | Sayles |
| 2003/0146836 | A1 | 8/2003 | Wood |
| 2004/0019464 | A1 | 1/2004 | Martucci |
| 2004/0078231 | A1 | 4/2004 | Wilkes |
| 2004/0172302 | A1 | 9/2004 | Martucci |
| 2005/0102167 | A1 | 5/2005 | Kapoor |
| 2005/0125068 | A1 | 6/2005 | Hozack |
| 2006/0084934 | A1 | 4/2006 | Frank |
| 2007/0006887 | A1 | 1/2007 | Frank |
| 2007/0135965 | A1 | 6/2007 | Nguyen |
| 2007/0290030 | A1 | 12/2007 | Fox |
| 2008/0003667 | A1 | 1/2008 | Jones |
| 2008/0030345 | A1 | 2/2008 | Austin |
| 2010/0106194 | A1 | 4/2010 | Bonutti |
| 2010/0248981 | A1 | 9/2010 | Shirazi |
| 2012/0234922 | A1 | 9/2012 | Sample |
| 2012/0241524 | A1 | 9/2012 | Blot |
| 2012/0318863 | A1 | 12/2012 | Kim |
| 2012/0325905 | A1 | 12/2012 | Kim |
| 2014/0048900 | A1 | 2/2014 | Keysar |
| 2014/0125482 | A1 | 5/2014 | Rigsby |
| 2014/0197951 | A1 | 7/2014 | Savarese |
| 2016/0212577 | A1 | 7/2016 | Dor |
| 2017/0098049 | A1 | 4/2017 | Sweeney |

FOREIGN PATENT DOCUMENTS

| | | | |
|---|---|---|---|
| KR | 100881986 | | 2/2009 |
| KR | 101019674 | | 10/2010 |
| KR | 20110096700 | | 8/2011 |
| KR | 200462233 | Y1 | 9/2012 |
| KR | 101197088 | | 11/2012 |
| KR | 200475044 | Y1 | 10/2014 |
| KR | 101637919 | | 7/2016 |
| KR | 101677943 | | 11/2016 |
| WO | 2016208784 | | 12/2016 |

OTHER PUBLICATIONS

Axisa, F., et al., "Design and fabrication of a low cost implantable bladder pressure monitor," 2009 Annual International Conference of the IEEE Engineering in Medicine and Biology Society, pp. 4864-4867 (2009).

Bazaka, K., and Jacob MV., "Implantable devices: issues and challenges," Electron, vol. 2, pp. 1-34 (2013).

Beck, H., et al., "50th Anniversary of the first successful permanent pacemaker implantation in the United States: historical review and future directions," Am J Cardiel, vol. 106, No. 6, pp. 810-818 (2010).

Fiandra, O., "The first pacemaker implant in America," Pacing Clin Electrophysiol, vol. 11, Issue 8, pp. 1234-1238 (1988).

Food and Drug Administration, Nov. 4, 2014, Retrieved from the Internet: URL: https://www.fda.gov/medicaldevices/.

Furman, S., "Early history of cardiac pacing and defibrillation," Indian Pacing Electrophysiology, vol. 2, No. 1, pp. 2-3 (2002).

Greatbatch, W., and Holmes, CF., "History of implantable devices," IEEE Eng Med Biol Mag, vol. 10, No. 3, pp. 38-41 (1991).

Gruda, MC., et al., "A System for Implanting Laboratory Mice with Light Activated Microtransponders," J. Am. Ass. Lab. Animal Sci., vol. 49, No. 6, pp. 826-831 (Nov. 2010).

Jiang, G. and Zhou, D.D., "Technology Advances and Challenges in Hermetic Packaging for Implantable Medical Devices," Zhou, DD and Greenbaum, ES, Implantable neural prostheses 2, Techniques and Engineering Approaches, pp. 28-61 (2010).

Johnson, J.A., "FDA regulation of medical devices," Congressional research service, Federation of American Scientists, pp. 1-33 (Jun. 25, 2012).

Kileny, PR, et al., "Effects of preoperative electrical stimulability and historical factors on performance with multichannel cochlear implant," Ann Otol Rhinol Laryngol, vol. 100, No. 7, pp. 563-568 (1991).

Larsson, B., et al., "Lessons from the first patient with an implanted pacemaker: 1958-2001," Pacing Clin Electrophysiol, vol. 26, Issue 1 Pt1, pp. 114-124 (2003).

Magjarevic, R., and Ferek-Petric, B., "Implantable cardiac pacemakers: 50 years from the first implantation," Zdravniški vestnik, vol. 79, No. 1, pp. 55-67 (2010).

Majerus, SJ, et al., "Low-power wireless micromanometer system for acute and chronic bladder-pressure monitoring," IEEE Transactions on Biomedical Engineering, vol. 58, Issue 3, pp. 763-767 (2011).

(56) References Cited

OTHER PUBLICATIONS

Mokwa, W., "Medical implants based on Microsystems," Measurement Science and Technology, vol. 18, pp. R47-R57 (2007).
Narasimhan, S., et al., "Implantable electronics: emerging design issues and an ultra light-weight security solution," Conf Proc IEEE Eng Med Biol Soc, pp. 6425-6428 (2010).
Olivo, J., et al., "Energy harvesting and remote powering for implantable biosensors," IEEE Sensors Journal, vol. 11, Issue 7, pp. 1573-1586 (2011).
Onuki, Y, et al., "A review of the biocompatibility of implantable devices: current challenges to overcome foreign body response," J Diabetes Sci Technol, vol. 2, No. 6, pp. 1003-1015 (2008).
Rajappan, K., "Permanent pacemaker implantation technique: Part II," Heart, vol. 95, No. 4, pp. 334-342 (2009).
Robinson, E.J.H., and Mandecki, M., "Distributed Decisions: New Insights From Radio-Tagged Ants," In: Ant Colonies: Behavior in Insects, Nova Science Publishers, Inc. (2010).
Shlegr, Z, and Egorov, A., "Implantable electric bladder stimulator used for neurogenic failures," Biomed Eng (NY), vol. 7, pp. 382-383 (1974).
Wilson BS, and Dorman MF., "Cochlear implants: a remarkable past and a brilliant future," Hear Res., vol. 242, pp. 3-21 (2008).
Wong, J. Y., et al., "Biomaterials: Principles and Practices," Boca Raton, FL: CRC Press., pp. 281 (2012).
Zoll, PM, "Resuscitation of the heart in ventricular standstill by external electric stimulation," N Engl J Med, vol. 247, No. 20, pp. 768-771 (1952).
Notice of Allowance dated Sep. 5, 2019 in U.S. Appl. No. 16/012,652 of Philip Sayles, filed Jun. 19, 2018, 13 pages.
Non-Final Office Action dated Oct. 3, 2019 in U.S. Appl. No. 16/534,450 of Philip Sayles, filed Aug. 7, 2019, 9 pages.
Non-Final Rejection dated Feb. 21, 2019 in U.S. Appl. No. 16/012,652 of Philip Sayles, filed Jun. 19, 2018, 10 pages.
Notice of Allowance dated May 28, 2019 in U.S. Appl. No. 16/012,652 of Philip Sayles, filed Jun. 19, 2018, 7 pages.

Table A: Exemplary Types of Implants (Particularly Prostheses)

- ABSORBABLE IMPLANTS
- ARTIFICIAL LIMBS
- AUDITORY BRAIN STEM IMPLANTS
- BIOPROSTHESIS
- BLOOD VESSEL PROSTHESIS
- BONE-IMPLANT INTERFACE
- BREAST IMPLANTS
- COCHLEAR IMPLANTS
- DENTAL IMPLANTS
    - DENTAL IMPLANTS, SINGLE-TOOTH
- DENTAL PROSTHESIS
    - CROWNS +
    - DENTAL ABUTMENTS
    - DENTAL CLASPS
    - DENTAL PROSTHESIS, IMPLANT-SUPPORTED
    - DENTAL RESTORATION, PERMANENT +
    - DENTAL RESTORATION, TEMPORARY
    - DENTAL VENEERS
    - DENTURES +
    - PALATAL OBTURATORS
    - PERIODONTAL PROSTHESIS
    - TOOTH, ARTIFICIAL
- ELECTRODES, IMPLANTED
    - DEFIBRILLATORS, IMPLANTABLE
    - IMPLANTABLE NEUROSTIMULATORS +
- EMBOLIC PROTECTION DEVICES
    - VENA CAVA FILTERS
- EYE, ARTIFICIAL
- FIDUCIAL MARKERS
- GLAUCOMA DRAINAGE IMPLANTS
    - MOLTENO IMPLANTS

FIG. 1A

HEART VALVE PROSTHESIS
HEART, ARTIFICIAL
    HEART-ASSIST DEVICES
IMPLANTS, EXPERIMENTAL
INTERNAL FIXATORS
    BONE NAILS
    BONE PLATES
    BONE SCREWS +
    BONE WIRES
    SUTURE ANCHORS
JOINT PROSTHESIS
    ELBOW PROSTHESIS
    HIP PROSTHESIS
    KNEE PROSTHESIS
    METAL-ON-METAL JOINT PROSTHESES
    SHOULDER PROSTHESIS
LARYNX, ARTIFICIAL
LENSES, INTRAOCULAR
MAXILLOFACIAL PROSTHESIS
    MANDIBULAR PROSTHESIS
ORBITAL IMPLANTS
OSSICULAR PROSTHESIS
PENILE PROSTHESIS
PROSTHESIS DESIGN
    PROSTHESIS COLORING
PUNCTAL PLUGS
SEPTAL OCCLUDER DEVICE
STENTS
    DRUG-ELUTING STENTS
    SELF EXPANDABLE METALLIC STENTS
SUBURETHRAL SLINGS
TISSUE EXPANSION DEVICES
TISSUE SCAFFOLDS
URINARY SPHINCTER, ARTIFICIAL

FIG. 1B

Inventory Control Form

*SET MISSING INSTRUMENTS
03.503.001 - Drill guide
03.503.032 Screwdriver Blade
* McCarthy Count Sheet SYNTHES CMF
SYNTHES CMF
To order: (800) 523-0322
SYNTHES CANADA
To order: (800) 668-1119

Screw strength gradient

Patient Information: PT. D.G.

Date: 5-17-16

Hospital: MAINE MEDICAL CTR - BRAMHALL

Titanium MatrixMANDIBLE

Implants

2.0 mm Titanium MatrixMANDIBLE Screws, self-tapping (1/pkg.) 47.25

| Qty | Part No. | Length | Qty | Part No. | Length |
|---|---|---|---|---|---|
| 1 | 04.503.405.01 | 5 mm | 2 | 04.503.412.01 | 12 mm |
| 3 (2) | 04.503.406.01 | 6 mm | | 04.503.414.01 | 14 mm |
| | 04.503.408.01 | 8 mm | | 04.503.416.01 | 16 mm |
| | 04.503.410.01 | 10 mm | | 04.503.418.01 | 18 mm |

2.0 mm Titanium MatrixMANDIBLE Locking Screws, self-tapping (1/pkg.) 88.83

| Qty | Part No. | Length | Qty | Part No. | Length |
|---|---|---|---|---|---|
| | 04.503.605.01 | 5 mm | 1 | 04.503.612.01 | 12 mm |
| | 04.503.606.01 | 6 mm | 2 | 04.503.614.01 | 14 mm |
| | 04.503.608.01 | 8 mm | | 04.503.616.01 | 16 mm |
| 2 | 04.503.610.01 | 10 mm | | 04.503.618.01 | 18 mm |

2.0 mm Titanium MatrixMANDIBLE Screws, self-drilling

| Qty | Part No. | Length |
|---|---|---|
| | 04.503.506.01 | 6 mm |
| | 04.503.508.01 | 8 mm |

2.0 mm Titanium MatrixMANDIBLE Locking Screws, self-drilling

| Qty | Part No. | Length |
|---|---|---|
| | 04.503.546.01 | 6 mm |
| | 04.503.548.01 | 8 mm |

2.4 mm Titanium MatrixMANDIBLE Screws, self-tapping (1/pkg.) 68.04

| Qty | Part No. | Length | Qty | Part No. | Length |
|---|---|---|---|---|---|
| 1 | 04.503.635.01 | 5 mm | 2 (2) | 04.503.442.01 | 12 mm |
| | 04.503.636.01 | 6 mm | 1 (1) | 04.503.444.01 | 14 mm |
| | 04.503.638.01 | 8 mm | | 04.503.446.01 | 16 mm |
| 2 (2) | 04.503.640.01 | 10 mm | | 04.503.448.01 | 18 mm |

Slotted Screw for Condylar Head Add-on System for MatrixMANDIBLE

| Qty | Part No. |
|---|---|
| | 04.497.001 |

2.4 mm Titanium MatrixMANDIBLE Locking Screws, self-tapping (1/pkg.) 108.99

| Qty | Part No. | Length | Qty | Part No. | Length |
|---|---|---|---|---|---|
| | 04.503.638.01 | 8 mm | | 04.503.644.01 | 14 mm |
| | 04.503.640.01 | 10 mm | | 04.503.646.01 | 16 mm |
| 1 (1) | 04.503.642.01 | 12 mm | | 04.503.648.01 | 18 mm |

2.0 mm Titanium MatrixMANDIBLE Emergency Screws, self-tapping (1/pkg.) 74.34

| Qty | Part No. | Length | Qty | Part No. | Length |
|---|---|---|---|---|---|
| | 04.503.465.01 | 5 mm | | 04.503.472.01 | 12 mm |
| 2 (1) | 04.503.466.01 | 6 mm | | 04.503.474.01 | 14 mm |
| | 04.503.468.01 | 8 mm | | 04.503.476.01 | 16 mm |
| | 04.503.470.01 | 10 mm | | 04.503.478.01 | 18 mm |

2.9 mm Titanium MatrixMANDIBLE Locking Screws, self-tapping (1/pkg.) 108.99

| Qty | Part No. | Length | Qty | Part No. | Length |
|---|---|---|---|---|---|
| | 04.503.668.01 | 8 mm | | 04.503.674.01 | 14 mm |
| | 04.503.670.01 | 10 mm | | 04.503.676.01 | 16 mm |
| | 04.503.672.01 | 12 mm | | 04.503.678.01 | 18 mm |

FIG. 4
(PRIOR ART)

OPERATING ROOM SITUATED, PARTS-INVENTORY CONTROL SYSTEM AND SUPERVISORY ARRANGEMENT FOR ACCURATELY TRACKING THE USE OF AND ACCOUNTING FOR THE ULTIMATE DISPOSITION OF AN INDIVIDUAL COMPONENT PART OF A COMPLETE IMPLANT WHICH IS THEN BEING SURGICALLY ENGRAFTED IN-VIVO UPON OR INTO THE BODY OF A LIVING SUBJECT

FIELD OF THE INVENTION

The present invention is generally concerned with the use of Complementary Metal Oxide Semiconductor (CMOS) chip technologies which are electronically able to broadcast a range of different RF signals; and is particularly directed to a parts-inventory control system and supervisory arrangement which accurately tracks the use of and precisely accounts for the ultimate disposition of at least some of the individual pieces which collectively are required to form a completely engrafted implant or implant construct, as each component part of that implant is being individually surgically inserted in-vivo at a preselected anatomic site upon or within the body of a living subject.

BACKGROUND OF THE INVENTION

A. In-Vivo Engrafted Implants

¶ Over the past six decades, the range and variety of implantable medical devices, engrafted biomedical objects, and articles of manufacture operative in-vivo have been technologically advanced through many major developments in science and product engineering; and such items have most especially benefited by the emerging fields of microelectronics, biotechnology, and biocompatible materials. From the earliest published medical reports in 1952 of biophysical devices for electrical heart stimulation, to the first commercialized wireless blood pressure measurement apparatus introduced in 2010, the medical quality of patients' lives has been greatly altered and improved with implantable devices and articles such as the implantable cardiac defibrillator, the cochlear implant, the implanted bladder stimulator, and the implantable wireless pressure sensor.

Historically, many such implantable medical devices and articles have been created and developed as manufactured fabrications which can sense and measure a physiological response in-vivo or which are able to actuate physiological organs in-vivo. More recently, with the super-miniaturization of electronic circuits and mechanical structures, many physicians, surgeons, and medical researchers have focused on the development of implantable real-time vital monitoring systems, which in-vivo can and will be continuously operated in sub-second time interval periods.

Such technological advancement for and established history of implant or implant constructs generally is briefly reported and summarily documented by the following representative scientific publications: Johnson J A, FDA regulation of medical devices. Congressional research service, Jun. 25, 2012, [Internet] Washington, DC, Federation of American Scientists, c2013; Jiang G and Zhou D D., Technology advances and challenges in hermetic packaging for implantable medical devices, In: Zhou D D, Greenbaum E S, editors, Implantable neural prostheses 2: techniques and engineering approaches, Berlin, Springer, 2010. pp. 28-61; Zoll P M, Resuscitation of the heart in ventricular standstill by external electric stimulation. N Engl J Med, 1952, 247:768-771; Greatbatch W, Holmes C F. History of implantable devices, IEEE Eng Med Biol Mag. 1991,10:38-41; Magjarevic R. & Ferek-Petric B., Implantable cardiac pacemakers: 50 years from the first implantation, Zdrav Vestn. 2010, 79:55-67; Larsson B, Elmqvist H, Ryden L, Schuller H. Lessons from the first patient with an implanted pacemaker: 1958-2001, Pacing Clin Electrophysiol. 2003, 26(1 Pt 1):114-124; Beck H, Boden W E, Patibandla S, Kireyev D, Gutpa V, Campagna F, et al. 50th Anniversary of the first successful permanent pacemaker implantation in the United States: historical review and future directions, Am J Cardiol. 2010, 106: 810-818; Rajappan K., Permanent pacemaker implantation technique: Part II, Heart 2009, 95:334-342; Fiandra O, The first pacemaker implant in America. Pacing Clin Electrophysiol. 1988, 11:1234-1238; Furman S. Early history of cardiac pacing and defibrillation, Indian Pacing Electrophysiol J. 2002, 2:2-3; Kileny P R, Zimmerman-Phillips S, Kemink J L, Schmaltz S P, Effects of preoperative electrical stimulability and historical factors on performance with multichannel cochlear implant, Ann Otol Rhinol Laryngol 1991,100:563-568; Wilson B S, Dorman M F., Cochlear implants: a remarkable past and a brilliant future, Hear Res. 2008, 242:3-21; Shlegr Z, Egorov A., Implantable electric bladder stimulator used for neurogenic failures. Biomed Eng (N.Y.) 1974, 7:382-383; Majerus S J, Fletter P C, Damaser M S, Garverick S L. Low-power wireless micromanometer system for acute and chronic bladder-pressure monitoring, IEEE Trans Biomed Eng, 2011, 58:763-767; Axisa F, Jourand P, Lippens E, Rymarczyk-Machal M, De Smet N, Schacht E, et al, Design and fabrication of a low cost implantable bladder pressure monitor, Conf Proc IEEE Eng Med Biol Soc 2009: 4864-4867; Mokwa W. Medical implants based on Microsystems, Meas Sci Technol. 2007;18:R47-R57; Narasimhan S, Wang X, Bhunia S., Implantable electronics: emerging design issues and an ultralight-weight security solution, Conf Proc IEEE Eng Med Biol Soc, 2010:6425-6428; Bazaka K, Jacob MV., Implantable devices: issues and challenges, Electron 2013; 2:1-34; Olivo J, Carrara S, De Micheli G., Energy harvesting and remote powering for implantable biosensors, IEEE Sens J., 2011, 11:1573-1586].

Nomenclature & Terminology

¶ Initially, it is important to recognize that there are many diverse types and different kinds of implants (or complete implant constructs) and transplants available today for surgical introduction and in-vivo juncture at a prechosen anatomic location in-situ, either topically upon on or embedded within the living body. Consequently, as the sophistication and complexity of the technology has continued to grow and expand, it now becomes evermore necessary to employ a proper nomenclature which is both technically accurate as well as is sufficiently precise in its meanings. In particular, in order to avoid ambiguities, misidentifications, and misunderstandings, each person must not only recognize what the correct nomenclature actually is, but also to employ all such names, titles, and terminology in an appropriate manner for communications with the ordinary skilled practitioner working today in this field.

As a first exemplary instance of such nomenclature criticality, attention is directed to the fundamental medical differences and major surgical distinctions existing between the terms 'implants' (or alternatively 'complete implant constructs') and 'transplants'. By long-established medical definition, an "implant " (or complete implant construct) is a broad phylum or order designation which includes many diverse member items; and via its broad encompassing scope of coverage, encompasses any kind and type of operational device, structural object and/or functional article which is artificially created or synthetically fabricated by man or machine, and which is subsequently surgically introduced upon on the surface or is engrafted within a living human or animal recipient body.

Consequently, all implants (and complete implant constructs as such) collectively are and cumulatively must be manufactured, synthesized, and fabricated items made by humans or machines, and which are intended to be and in fact are subsequently surgically engrafted inside the living body or upon the skin surface of a living subject. An incomplete, but illustrative, representative listing of some conventionally known and used implants and complete implant constructs is provided by Prior Art FIG. 1 via Table A.

In major contrast and marked difference, a 'transplant' by medical definition is and must be a naturally occurring and pre-existing body part—i.e., a native tissue, structure, organ, or organelle created in-vivo and naturally grown within the living body, and which is excised from a donor body for subsequent surgical placement in a recipient's body. As a direct corollary requirement, all items properly termed a 'transplant' are and must be obtained solely either by surgical dissection from a recently deceased corpse or by surgical excision from a presently living (human or animal) donor body. Accordingly, by definition, all transplants as such are limited to and must be directed towards the transfer of a naturally occurring tissue, organ, or body part from a donor body to a recipient body.

In addition, as a second exemplary instance of precise nomenclature in title designations, one will realize and accept that there are several well-established categories or divisions as such within the phylum membership of implants and implant constructs. One well known specific division of implants encompasses a very broad range of items known as 'prostheses'—i.e., those types of devices, objects and articles intended to serve as a complete functional artificial replacement for a now missing, or degraded, or defective body part(s).

Furthermore, several other well-established categories and accepted divisions of surgical implants and implant constructs are also conventionally known; and some of these other divisions are traditionally named or designated as "drug delivery devices", "sensory articles", "fixation hardware", and "repair structures" respectively. Each of these alternative divisional appellations constitutes and includes a diverse host of different member items; and each of these categories is typically concerned with one general purpose and goal. Consequently, each one of these four divisions is able alternatively: To deliver a desired medication in-situ; or to sense and monitor physiological body functions in-vivo; or to provide structural support for the native anatomy; or to help injured or weakened tissues, bones, muscles and/or organs heal over time. Clearly, each of these commonly recognized categories and divisions provides a broad membership of different medical items and offers a wide range of alternative in-vivo functions—from which the surgeon can choose at will in order to meet and satisfy the particular medical needs of the individual patient.

Thus, for all these reasons, the terms "implant" and "complete implant construct" as employed herein are synonymous and interchangeable; and will consistently indicate and uniformly serve as the broadest possible name and title for the operative entity engrafted in-vivo; and will also provide the greatest scope of coverage for its encompassed member subsets and included divisions. In particular, these appellations explicitly encompass and incorporate all the conventionally known divisions and subsets—e.g., "prostheses", "drug delivery devices", "fixation supports", and "repair structures" as such—without regard to the member type, item kind, individual features, operative functions, and envisioned medical application(s).

Accordingly, the only true rule and requirement for any implant and complete implant construct as such is that the particular item always be a fabricated medical device, or object, and/or functional article which has been created by human effort and design; and which, after surgical Introduction and juncture upon or into a living subject body—then serves in-vivo as a functional substitute and replacement for a presently defective or missing natural anatomical or biological part; or then acts to support a damaged existing biological or biochemical structure within the living body; or then operates in-vivo to enhance the poor functionality of an existing native tissue, organelle, or organ.

Properties & Characteristics Commonly Shared By Implants

Several traits and attributes pertain to and are commonly shared by the diverse membership of medical/surgical implants and implant constructs as a broad phylum without regard to whether its members are individually devices, or objects, or articles. Among these distinguishing properties are the following:

- The exposed exterior surface of implants and implant constructs that will make contact in-situ with native body cells, living tissues and flowing bodily fluids are often made (at least in part) of a biochemically inert and/or chemically neutral durable substance such as titanium, silicone, or apatite—the biocompatible material choice depending upon what is to be the intended purpose, activity or function of the item [see for example, Wong, J. Y.; Bronzino, J. D.; Peterson, D. R., eds. (2012), *Biomaterials: Principles and Practices, Boca Raton, FL.: CRC Press*. p. 281].
- In many instances, surgically introduced implants and implant constructs will contain and/or be in direct communication with one or more electronic sensors, integrated circuits, central processing units, and battery power systems—as illustrated and exemplified by artificial pacemakers and cochlear implants [see for example: Narasimhan S, Wang X, Bhunia S. Implantable electronics: emerging design issues and an ultra-light-weight security solution. Conf Proc IEEE Eng Med Biol Soc. 2010;2010:6425-6428].
- Some surgically introduced implants and implant constructs are bioactive articles—as illustrated and exemplified by subcutaneous drug delivery devices, implantable time-release medicaments, and drug-eluting stents [see for example: FDA.org/medicaldevices, Food and Drug Administration. 4 Nov. 2014].
- Some kinds of surgical implants and implant constructs are made from skin, bone, cartilage, or other naturally occurring body tissues. In contrast, many other types are made from biocompatible metal, plastic, ceramic or other inorganic materials. A minority percentage of humans also have mild to severe body reactions to the particular materials used in certain implant devices and objects [see for example: Onuki Y, Bhardwaj U, Papadimitrakopoulos F, Burgess D J, A review of the biocompatibility of implantable devices: current challenges to overcome foreign body response, *J Diabetes Sci Technol,* 2008, 2:1003-1015].

Surgical implants and implant constructs can alternatively either be placed in-vivo permanently; or they can be temporarily positioned in-vivo at a prechosen anatomic site, and later be removed once they are no longer needed by the patient. For example, stents or hip joint implants are intended to be permanent grafts. In comparison, chemotherapy ports or structural screws used to hold broken bones together for repair can afterwards be surgically removed after bone healing and when they are no longer medically needed [see for example: Greatbatch W, Holmes C F. History of implantable devices, *IEEE Eng Med Biol Mag,* 1991,10:38-41].

The Diversity of Medical Applications for Implants as a Whole

Historically, the phylum of implants (and complete implant constructs) as a whole has been roughly separated into different groupings which are separated by and vary in their intended in-vivo function(s) and/or expected medical application(s). In point of practical fact, such medical application groupings are merely convenient designations which are neither precisely maintained, nor have singular or compulsory distinctions. Nevertheless, such medical application groupings generally serve quite well most of the time as a convenient expedient by which to separate the many types and kinds of available implants and complete implant constructs for most surgical purposes. Thus, merely as a matter of acknowledged usage and ordinary surgical practice, some of the representative designations of these medical application groupings are the following:

1. Sensory & Neurological Items

Sensory and neurological devices are fabricated articles used for treating pathologies and disorders affecting the major senses and the brain, as well as for treating many neurological diseases. Such articles are those predominately used in the treatment of optical nerve conditions such as cataract, glaucoma, keratoconus, and other visual impairments; auditory nerve disorders such as otosclerosis and other hearing loss issues, as well as middle ear diseases such as otitis media; and neurological pathologies and disorders such as epilepsy, Parkinson's disease, and treatment-resistant depression. Well known examples currently include the intraocular lens, intrastromal corneal ring segment, cochlear implant, tympanostomy tube, and neurostimulator.

2. Cardiovascular Devices

Cardiovascular medical devices are implants and implant constructs used in cases where the heart, its valves, and the rest of the circulatory system is abnormal or in disorder. They are used to treatment specific cardiac conditions such as heart failure, cardiac arrhythmia, ventricular tachycardia, valvular heart disease, angina pectoris, and atherosclerosis. Well known examples of these items include the artificial heart, artificial heart valve, implantable cardioverter-defibrillator, cardiac pacemaker, and coronary stent.

3. Orthopaedic Structures

Orthopaedic implants and implant constructs help alleviate medical issues involving the bones and joints of the living body. Such items are used to treat bone fractures, osteoarthritis, scoliosis, spinal stenosis, and chronic pain. Common examples include a wide variety of pins, rods, screws, and plates used to anchor fractured bones over the time required for healing.

4. Contraceptives

Contraceptive implants and implant constructs are primarily used to prevent unintended pregnancy and to treat medical conditions such as non-pathological forms of menorrhagia. Typical examples include copper- and hormone-based intrauterine devices.

5. Cosmetic Articles

Cosmetic articles, and most often cosmetic support structures, attempt to bring some portion of a degraded living body back to a socially acceptable aesthetic norm. Such items are used as a follow-up surgery to mastectomy due to breast cancer; for correcting some forms of disfigurement; and for modifying aspects of the body (as in buttock augmentation and chin augmentation). Common examples include the breast implant, nose prosthesis, ocular prosthesis, and injectable filler sites; and the treatment of such diverse medical conditions such as gastroesophageal reflux disease, gastroparesis, respiratory failure, sleep apnea, urinary and fecal incontinence, and erectile dysfunction.

B. Conventional Operating Room Inventory Control Procedures for Surgically Engrafting Implants (a). Because the present invention is a substantial improvement and major advance in inventory control which identifies the actual use and ultimate disposition of specific component parts for an engrafted medical implant and implant constructs - it is deemed both necessary and appropriate to consider briefly what in fact is the conventional practice and current procedure used today by surgeons, surgical nurses, and surgical technologists/assistants in the operating room theater for counting, tracking, and accounting for each individual implant component pieces during the surgery.

For illustrative and descriptive purposes only, one will recognize that the individual component parts of the operational implant (or complete implant construct) which is to be engrafted in-vivo must include, but certainly is not limited to, the following:

- Metallic hardware implants and implant constructs or 'fixations' including titanium or stainless steel plates, screws, and nails, and wires used for skeletal repair or bone reconstruction;
- Anatomic implants and complete implant constructs of varying types—i.e., synthetic joints for the hip, elbow, knee or ankle which are comprised of stainless steel, synthetic compounds, and other durable solid materials;
- Repair implants and implant constructs for structural support in-vivo—such as collagen meshes, de-cellularized porcine and bovine skin preparations, and other kinds of embeddable and topical articles used for repair and healing.

(b). Typically, much of the metallic hardware constituting a requisite component part is surgically necessary for achieving a correct physical joining and customized grafting in-situ of the operational implant as a whole. For this reason, such metallic hardware is often individually housed in a modular kit or tray as hardware inventory; and appears ready for use as prepared sets of individual items which are collectively contained within the multiple shaped wells of a sterilized modular kit or tray. This modular kit housing format for hardware is highly preferred by the surgical team within the limited spatial confines of an operating room; and this housing format provides the surgeon with a sufficiently wide range of part choices in alternative sizes, shapes, and configurations that will then be available to best fit and meet the immediate surgical needs of the individual patient.

A typical and representative example of this sterilized modular kit array of parts format is illustrated by Prior Art FIGS. 2A and 2B respectively. As seen in Prior Art FIG. 2A, a large range and variety of Philips screws are provided in several alternative different lengths and diameters within the multiple containment wells of the modular kit. In a similar fashion as illustrated by Prior Art FIG. 2B, a variety of alternative length metallic support arms are individually housed within the shaped wells of a second modular kit, wherein the available series of support arms differ in their individual length and width dimensions.

These multiple sets of alternatively-sized component parts are organized within the modular kits of Prior Art FIGS. 2A and 2B respectively as a parts-inventory collection—wherein each individual component part resides and is to be found at one location within in the respective modular kit or tray. If and when actually used during the surgery, each of the presently used component parts will subsequently be individually replenished after the kit is washed post surgery—in order to provide a full complement of alternative hardware sizes and a complete inventory modular kit for the next surgical graft occasion.

Equally important, the inventory part contents of the modular kits or trays shown by Prior Art FIGS. 2A and 2B respectively must be and are subjected repeatedly and routinely to harsh cleaning cycles; and then to sterilization (by dry heat, or steam, or gas, or gamma radiation) in advance of the next intended surgical use occasion. The contents of these prepared-in-advance modular kits thus serves to provide the surgeon with at least a complete inventory of metallic hardware parts, which may or may not be needed on each surgical implant occasion.

Thus, the typical routine is this: After each surgical use occasion, all the then depleted parts in the inventory of these modular kits will be individually identified; and each of the missing parts will be individually restocked by hand with appropriate replenishment component pieces, in the numbers and sizes as are required to result in a complete parts inventory. In this manner, the full range and intended variety of individual hardware component parts presented by the modular kit for engrafting a complete implant are regenerated and completely restored.

It is self-evident, therefore, that after each depleted parts replenishment event, the full inventory contents of these modular kits can and will be available for use over and over again indefinitely—so long as the hardware parts inventory for each modular kit continues to be properly restocked after each surgical use.

(c).Typically, the surgeon(s) will work with a surgical technologist (hereinafter "ST"), who is also dressed in sterile garb and stands in the aseptic operating field with the surgeon, as is illustrated by Prior Art FIG. 3. The functional role of the ST is to hand sterile instruments, supplies, and the inventory part contents of the modular kits (shown by Prior Art FIGS. 2A and 2B) to the surgeon(s) as needed and/or requested. For this reason, in conventional operating room practice and procedure, the necessary sterile surgical instruments and tools, implant supplies and component part modular kits are routinely placed on a cloth covered mayo stand—i.e., a portable table which is typically positioned directly over the patient as shown by Prior Art FIG. 3. The ST hands whatever is required to the surgeon as he asks for it; and each item requested by the surgeon is identified and recorded by the ST to create and maintain inventory control of component parts during the operation.

Summary of the Conventional Surgical Procedure

In order to understand fully and appreciate properly the nature and demands of this conventional practical and procedure, an accurate summary description is presented below:

- As the surgeon selects or calls for individual component pieces from the items on the mayo stand, the ST will hand them to the surgeon as requested.
- The ST will then take a sterilized pen or marker; and by hand write down the component part identification number associated with each tangible piece then being used as a component directly on the mayo cover or upon a piece of sterilized paper. It will be recognized and noted that at least some of the individual component parts have long complex identification part numbers corresponding to them.
- At the end of the surgical operation, the surgeon will be finished with the physical engrafting of the completely constructed implant into the living body of the patient. It is only at this point near the end of the surgery that the ST will orally recite and call out each one of the component part identity numbers which corresponds to the individual component parts actually in the patient and used to engraft the implant or implant construct surgically.

This oral recitation of multiple component part identity numbers is made from the hand-written listing that ST has previously prepared; and this recitation is made within the operating room environment to a sales representative or a circulating nurse - who then themselves write down and record the recited identity part number information onto a pre-printed form traditionally called and "Inventory Control Sheet", which is illustrated by Prior Art FIG. 4. This "Inventory Control Sheet" of Prior Art FIG. 4 in turn serves to organize the recorded random information that the ST has previously written down on the mayo stand.

- After the data entered onto the "Inventory Control Sheet" of Prior Art FIG. 4 is confirmed by the ST as being complete and correct, the hand written sheet is then taken by the circulating nurse to a computer station (which typically is also within the operating room theatre). The circulating nurse will then manually enter all the hand-written identity part number information into a CPU database as the official record of what the implant surgery involved and used. This is a tedious and very laborious task; takes on average at least 10-15 minutes to complete; and unfortunately is subject to much human error.

For convenience and greater appreciation, the entire conventional practice and surgical procedure as a whole is summarily illustrated by the flow chart of Prior Art FIG. 5.

C. RFID Transponders

One recognized class of CMOS technology is radio frequency identification data (RFID) circuitry—an automatic identification technology whereby digital data encoded in a transponder or RFID "tag" is captured by a remotely located reader using radio waves. RFID technology has been conventionally known and used since about 1970; but it has generally been too cumbersome and expensive to use on a large scale, and thus has not been a commercial success to date.

Ж Since its earliest applications, RFID tags have long been used to detect and track large-sized tangible items that had to be shipped over long distances (such as livestock, railroad cars, and airline freight). These $1^{st}$ generation radiofrequency labels were all 'inductively coupled RFID tags'—i.e., very complex units formed of metal coils, antennae and glass; but which lacked any internal power source. As then designed, such inductively coupled RFID tags were powered by a magnetic field generated by a separate, but closely located, discrete RFID reader which generated an external magnetic field and inducted electric current flow within the tag components. The term "inductively coupled" refers to this process wherein the magnetic field of the RFID reader inducts an electric current in the tag circuitry.

Subsequently, a $2^{nd}$ generation radiofrequency transponder was developed, which has come to be known as the 'capacitively coupled tag'. These $2^{nd}$ generational improvements were disposable RFID tags that functioned as universal identifiers; and were made for direct attachment to less expensive merchandise that required shipping. For this purpose, all 'capacitively coupled tags' use conductive carbon ink instead of metal coils to transmit data. Typically, the conductive carbon ink was printed on paper labels, which were then scanned by external readers located nearby.

The most recent innovations are a $3^{rd}$ generational improved RFID tag which encompasses and exists in not less than three structurally different construction formats, which are: The active, semi-passive, and passive formats.

Active and semi-passive RFID tag formats each use internal batteries to power their electronic circuits. An active RFID tag uses its battery power to broadcast radio waves to a remotely located reader/detector; whereas a semi-passive RFID tag relies on the remote reader/detector to supply the initiating radio signal for the tag to respond. The purpose of the internal battery in the semi-passive tag is to boost the effective operating range of the tag and to support additional feature—such as operation with lower radio signal strengths and sensing operations that require continuous power. Data from active and semi-active tags collected by remotely located readers/detectors is then passed through one or more communication interfaces (cable or wireless) to host computer systems; and is then passed to computer systems for decoding, interpretation, storage, and action. Alternatively, electric power may be supplied externally—e.g., by means of a car battery.

In marked contrast, passive RFID transponders rely entirely on the remotely located RF reader as their sole power source. Consequently in such passive systems, the RFID tag is formed solely of an antenna and a silicon chip that includes basic modulation circuitry and a non-volatile memory. Moreover, because passive RFID tags rely entirely on the electromagnetic field generated by the external RF reader as their sole power source, these tags are very limited in their broadcast distances. Nevertheless, passive RFID tags can have their emitted RF signals be read up to separation distances of about 20 feet (six meters).)

Ж Despite these structural design differences, it will be noted and appreciated that all three RFID tag format variants (i.e., active, semi-passive and passive RFID tags) provide very similar operational features and characteristics, which typically include the following:

All three variant tag construct formats are composed of a microchip and an antenna; but only the active and semi-passive formats include an internal battery for power. Typically, a RFID transponder unit contains a semiconductor chip having RF circuits, logic, memory, and an external antenna. The RFID transponder often includes a collection of discrete components—such as capacitors and diodes; a battery in the case of active transponders; a substrate for mounting the components, interconnections between components; and a means of protective physical enclosure. See for example U.S. Pat. Nos. 9,361,568; 9,370,401; 9,405,950; 9,418,263; 8,476,689; 8,576,050; 8,587,406; 8,596,544; 8,616,459; 8,628,018; and 8,636,220 respectively.

All three variant construct formats are manufactured by mounting the individual elements to a circuit card. This is done by using either short wire bond connections or soldered connections between the board and the circuit elements: chip, capacitors, diodes, and antenna. The circuit card may be of epoxy-fiberglass composition or ceramic. The external antennas are generally loops of wire soldered to the circuit card or consist of metal etched or plated on a circuit card. The whole arrangement may be enclosed in a plastic box or molded into a volumetric three-dimensional plastic package. See for example U.S. Pat. Nos. 6,147,662 and 6,177,859.

All three variant construct formats have their data stored within a microchip which waits to be electronically read. RFID tags comprise an integrated circuit (IC) attached to an antenna, plus some protective packaging as determined by the application requirements. Specific identification data is stored in the integrated circuit and is sent through the antenna as a responsive or reflected RF signal to a remotely located RF signal reader. See for example U.S. Pat. Nos. 3,967,202; 4,614,945; 4,816,839; 5,528,222; 5,682,143; 5,786,626; 5,825,298; 5,874,902; 5,974,078; 6,104,281; and 8,350,704.

All three variant construct formats require that the remotely located reader pick up the tag's broadcast radio waves and interpret the emitted radiofrequencies as meaningful data. Each RFID transponder unit contains individual coded information which relates to and identifies the object bearing the tag. The remotely located reader of the system sends an initial RF signal over a set distance to the transponder unit. The external antenna of the discrete transponder unit receives the initial RF signal from the remotely located reader; and backscatter modulates the received RF signal with data temporarily or permanently stored in the transponder (such as data indicating the identity and contents of the object to which the transponder is attached). This event, in turn, then produces a sequence of RF response signals in accordance with the transponder's individual code; and this modulated RF response signal is sent back via the external antenna to the remotely located reader. After the RF response signal is received, the remote reader decodes these RF signals to obtain the information and data sent from the transponder unit. See for example, U.S. Pat. Nos. 5,641,634; 7,195,149; 7,328,837; 5,892,458; 7,135,977; and 8,587,410.

Traditionally, RFID transponders are all modestly large articles of manufacture; and as such are intended to be attached to or incorporated into any relatively large object or jumbo sized item—e.g., a bulky or hefty product (suitcases, shipping containers, and kitchen appliances), a living animal maintained as a food source (cattle, pigs, and sheep), or the tangible form of a transportation vehicle (autos, railroad cars, and aircraft). Consequently, there is no such thing as a miniaturized FRID transponder unit; and to date, it has been impossible to make a truly small-sized RFID transponder as such. For all these reasons, all RFID transponders regardless of type are of-necessity modestly large in both dimensional size and overall volume; and consequently cannot be fitted onto any small-sized area or minimal available surface.

In addition, it has long been recognized that the maximum travel distance over which the RF response signal of the transponder can be broadcast is directly proportional to the power of the available battery and the length of the external antennae. Thus, the RFID response signal broadcast distance is generally very short, and is typically measured in mere meters or feet. As a result, the transponder's RF signal broadcast demands that the included battery be as large as possible, and that the tag's antennae be dimensionally long in size in order to that the broadcast signal travel even a short distance of 30 meters.

Representative Examples of Medical Applications Using Conventionally Known RFID Transponders A host of biomedical designers and biophysical engineers have sought and developed a variety of alternative medical applications—all of which use RFID transponders, central processing units and their associated electronic circuitry, together with a variety of RF recorders and visual displays. Merely illustrating and representing their medical application purposes, goals, and results are the following efforts.

U.S. Pat. No. 8,996,393 of R. A. Sobie Issued Mar. 31, 2015

This patent describes a system of controlling inventory in a medical facility which comprises: a medical treatment area within a medical facility having a network, the medical treatment area and network being configured such that the network can determine that a wireless medical device is within the medical treatment area and the medical treatment area is assigned to a patient; a plurality of wireless medical devices inventoried by the medical facility, each inventoried wireless medical device having a medical device record—wherein the network is configured to detect and identify automatically a wireless medical device upon introduction of the wireless medical device into the medical treatment area, determine whether a medical device record exists for the newly detected wireless medical device, create a medical device record if the newly detected wireless medical device does not have a medical device record, and assign the newly detected wireless medical device to the patient to whom the medical treatment area is assigned.

U.S. Pat. No. 8,717,430 of Simon et al. Issued May 6, 2014

This patent provides a system for performing a medical procedure on a patient. The system presents an imaging head defining a field of view relative to the patient; and includes at least one transmitter that emits at least one signal in the field of view, and at least one receiver that receives at least one reflected signal from the field of view. The reflected signal received is based on at least one electrical property of at least one material in the field of view. The system can further include a workstation, which can determine the location of at least one boundary of the material within the field of view; as well as an image display of the location at the boundary.

U.S. Pat. No. 8,663,120 of Markowitz et al. Issued Mar. 4, 2014

This patent reveals a method and apparatus for mapping a structure and operates to identify a plurality of locations in a mapping instrument. The mapping instrument can include one or more electrodes that can sense a voltage which can be correlated to a three dimensional location of the electrode at the time of the sensing or measurement. In this manner, a map of an area or volume can be determined based upon the sensing of the plurality of points without the use of an imaging device. An implantable medical device can then be navigated in-situ relative to the mapping data.

U.S. Pat. No. 8,660,640 of Markowitz et al. Issued Feb. 25, 2014

This patent discloses a method of determining a position of an instrument in a patient comprising moving at least a first position element and a second position element with the instrument into a volume of the patient; determining a position of the instrument with only a position sensing system—including providing a set of axis generation electrodes on an exterior surface of the volume establishing an axis and a conductive path therebetween; and injecting a current into the volume between the set of electrodes and generating a voltage gradient between the set of electrodes; evaluating an electrical property with the first and second position elements mounted on the instrument; determining a position of the first and second position elements within the volume based on the evaluated electrical property; determining a scalar distance between the first position element and the second position element on the instrument; evaluating the determined position of the first and second position elements based on the scalar distance to correct for a distortion of the injected current between the set of axis generation electrodes in the patient to determine a corrected position determination; and displaying a graphical representation of the corrected determined position of the first and second position elements.

U.S. Pat. No. 8,165,658 of Waynil et al. Issued Apr. 24, 2012

This patent discloses a system for positioning a guide relative to an anatomy is provided. The system can include a base adapted to be coupled to the anatomy, and a guide that can move relative to the base. The system can include at least one tracking device that can be coupled to the base and the guide; and a tracking system that tracks a position of the tracking device. The system can include a navigation system that determines a position of the base and the guide relative to the anatomy, and whether the position of the base and the guide are in a desired position. The system can also include a display, which can display at least one icon superimposed on the image of the anatomy that graphically indicates a manipulation of the guide required to move the guide into the desired position.

U.S. Pat. No. 8,027,632 of Mazar Issued Sep. 27, 2011

This patent discloses systems and methods for the selective prevention of data transfer from a medical device to allow the patient to have privacy when desired. These systems and methods provide medical devices that can be instructed in various ways to stop recording data and/or transmitting data to external devices and systems. These systems and methods also provide external repeater devices that can also be instructed in various ways to stop recording data being received, stop forwarding data that is being or has already been received, and/or to stop soliciting data from the medical device.

U.S. Pat. No. 7,698,156 of Martucci et al. Issued Apr. 13, 2010

This patent reveals a system and method for uniquely identifying data streams associated will medical equipment. The system may be implemented in a variety of ways—including as a combination of a medical device, a data stream identifier, and a medical device identifier. The medical device generates a plurality of data streams; and the data streams are uninterrupted transmissions of data from the medical device. The data streams can also include information regarding the operation of the medical device.

U.S. Pat. No. 7,585,302 of Revie et al. Issued on Sep. 8, 2009

This patent discloses an instrument for implanting a sensor in a body part. The sensor has at least one cord extending therefrom which is connected to an external device; and includes a guide sheath for defining a path to the surface of the body part through overlaying soft tissue—the sheath having a bore extending along its length between first and second open ends through which the tool can pass and has a slot that extends along its length between its first and second open ends.

U.S. Patent Application Publication No 20070290030A1 of Fox et al. Published on Dec. 20, 2007

This publication describes a system and method in a computerized healthcare environment for updating supply inventory data to reflect the use of a medical supply item. The system comprises a patient identifier for identifying a particular patient, and a scanned supply item identifier for identifying a specific supply item for use with that patient. The recorded use of the scanned supply item is indicated in an inventory database.

U.S. Patent Application Publication No 20070135965A1 of Nguyen et al. Published on Jun. 14, 2007

This publication discloses a system and method for storing items and tracking usage of items in a user configurable medication dispensing cabinet. Items are stored in a tray or drawer having user-adjustable storage spaces. A graphical user interface comprising a touch screen enables users to rapidly customize the layout of storage spaces, which allows a wide variety of shapes and sizes of items to be stored in the tray.

U.S. Patent Application Publication No 20070006887A1 of Frank Published on Jan. 11, 2007

This publication reveals a tracking system for prosthetic and implantable devices. This system includes, in combination, a prosthetic or implantable device and an RFID transducer fixed to the device which has lot identification information stored therein. A wand is provided which is capable of scanning the RFID transducer and reading the recorded information. Means are also provided for storing the read information.

U.S. Pat. No. 6,925,447 of McMenimen et al. Issued Aug. 2, 2005

This patent provides a medical device production and supply information management system which is synchronous with manufacturing, planning and scheduling, product consumption forecast, and component purchase; and enables just-in-time inventory control at the manufacturing facility, vendor stocks, material/product tracking, distribution and shipping management; and thereby reduces inventory at all points in the product manufacturing, distribution/delivery chain.

U.S. Patent Application Publication No. 20050102167A1 of A. K. Kapoor Published on May 12, 2005

This publication is concerned with provisioning and controlling medical instruments using wireless data communication. This invention teaches a method of automating some of the tasks requiring continuous data collection at the patient bedside in a hospital in a manner which significantly reduces the chances of error in providing treatment. These tasks include provisioning of the IV pumps or other fluid infusion pumps or feed pumps; oxygen delivery systems; and gathering, recording, storing, and analyzing signals from an ECG machine, or pulse oxymeter, or any other medical device.

U.S. Patent Application Publication No. 20040172302A1 of Martucci et al. Published on Sep. 2, 2004

This publication describes a system and method for comparing medical device settings to orders within a healthcare system. This method for verifying medical device settings within a healthcare system comprising the steps of transmitting data relating to operational parameters from the medical device to a first computer; storing data relating to an order in a memory of the first computer; and, comparing at least one of the operational parameters sent from the medical device to at least a portion of the order.

U.S. Patent Application Publication No 20040019464A1 of Martucci et al. Published on Jan. 29, 2004

This publication discloses a system and method for identifying data streams associated with medical equipment. This system for identifying data streams comprises a medical device generating data streams, the data streams being transmissions of data from the medical device, wherein the data streams include information regarding the operation of the medical device; a data stream identifier generating a unique data tag; a medical device identifier configured to generate a medical device tag upon receipt of a request from an external computer, the medical device tag including information to uniquely identify the medical device; and, a bridge configured to attach the unique data tag to the data stream, the bridge configured to provide the medical device tag to the external computer, wherein the data stream identifier and the medical device identifier are secured to the medical device.

U.S. Patent Application Publication No 20040078231A1 of Wilkes et al. Published on Apr. 22, 2004

This publication recites a system and method for facilitating and administering treatment to a patient, including clinical decision making, order workflow and integration of clinical documentation. This system is employed for facilitating documentation preparation utilizing preexisting material to improve treatment of the patient, the system comprising: a processor; a configuration module; a memory operably connected to the processor; and a record of encounters stored in the memory, wherein the configuration module, processor, and memory cooperate to generate an order utilizing the record.

Photovoltaic-Cell Powered Transponders

More recently, an entirely different class of miniature electronic transponders have been developed which utilize one or more internal photovoltaic cells to provide electric power for the integrated chip circuitry. The generation of such photovoltaic cell-activated chip transponders concomitantly permits the manufacture of miniature electronic transponder units, which have much smaller dimensions and volume than their predecessor RFID transponders.

For example, a monolithic photovoltaic cell containing electronic transponder unit which includes a transmitting antenna is disclosed by U.S. Patent Publications Nos. 201440048900; 20120325905; 20120318863; 20120241524; and 20120234922—as well as by U.S. Pat. Nos. 5,641,634; 6,590,150; and 7,791,481 respectively [whose published texts are individually expressly incorporated by reference herein] provides a marked reduction in size and volume for the functional unit.

Other improvements in miniature electronic transponders which utilize photovoltaic cells to provide electric power for the chip circuitry are represented by U.S. Pat. Nos. 7,633,111; 7,098,394; 7,053,294; 7,915,517; 8,089,285; 8,353,917; 8,574,946; 8,552,470; and 8,624,294—whose published texts are individually and collectively expressly incorporated by reference herein.

All such photovoltaic cell-activated chip transponders constitute and operate as a radio frequency identification device wherein electric power is supplied by the conversion of light radiation energy (natural or artificial) into direct electric current using internally placed photovoltaic cells, such as solar cells. In this manner, the photovoltaic cell is used in place of one or more internal batteries; or in place of RF energy harvesting circuits (rectification of the RF signals sent by the remotely located transceiver or reader); or in combination with either or both of these conventionally known sources of energy.

§ The photovoltaic cell-activated integrated chip transponder is oriented for use with a remotely located interrogator device, reader apparatus, or transceiver unit; and typically comprises a circuit (preferably an integrated circuit) configured to send a responsive signal (containing information to be sent to the reader) in response to an initiating RF signal (either unmodulated or modulated) sent from the remote interrogator/reader/transceiver. A communication antenna is electrically coupled to the transponder's electronic circuitry for wireless RF signal communication with the remotely located interrogator/reader/transceiver. The transponder's emitted response RF signal typically will include specific identification information and related data which is then received and decoded by the interrogator/reader/transceiver.

§ The photovoltaic cell-activated chip transponder can store any and all information that is deemed to be useful for the particular organization, institution, or business. The encoded data and stored information held within the photovoltaic cell-activated chip transponder can be updated as often as the prevailing conditions change; and subsequent signal communications can keep the human operator apprised of all current or recent changes.

§ Typically, one or more photovoltaic cells suitable for converting light radiation into electrical energy and providing electrical power to the chip electronic circuit will exist within the dimensional confines of a single transponder unit. A transponder constructed using a photovoltaic cell for operational power can have all the attributes and advantages of a traditional passive transponder unit (i.e., unlimited life, small size, low cost, etc.); with the added advantages of an increased range of communication distance; and may be used for a variety of different high performance applications.

§ Photovoltaic cell containing transponders also provide major advantages over their predecessor RFID types owing to their operational inactivity in the absence of external light illumination. Thus, if and when desired, a narrowly focused laser light source can and will activate only a single photovoltaic cell transponder unit at a time, even when many other transponders are present within the same use environment. Only the single illuminated photovoltaic cell transponder unit will transmit information and data, while all the other transponder units in the same locale will remain functionally inactive. This capability and reduction in the total number of signal transmitting transponders significantly reduces the background noise level, thereby making the return RF signal easier to detect.

However, if the user wishes the illuminating light to be more broadly applied, any desired total number of photovoltaic cell activated transponders will collectively respond in unison. In this manner, the light energy source can be adjusted to control precisely which individual photovoltaic cell transponders and how many total photovoltaic cell transponder units will be activated and respond on any use occasion.

Some Known Photovoltaic Chip Medical Applications

Some recent exemplary medical applications using photovoltaic cell transponder units are represented and illustrated by the following.

U.S. Pat. No. 9,370,401 of P. W. Sayles Issued on Jun. 21, 2016

This patent describes a millimeter-sized recognition signal badge and identification system for accurately discerning and sorting among similar kinds, shapes, and sizes of surgical instruments. This signal-identifying badge and operative system recognizes, differentiates and distinguishes among the many kinds, shapes and sizes of surgical instruments and tools commonly used today for human and veterinary surgeries and in scientific research. The signal-identifying badge is a discrete millimeter-sized article of manufacture which can be easily affixed to an exposed surface of any type, any configuration and any dimension of surgical instrument or tool; and includes a well-cushioned and protected photovoltaic cell-integrated chip transponder unit embedded within a safeguarding three-tier stack construct.

U.S. Pat. No. 9,313,558 of Mandecki et al. Issued on Apr. 12, 2016

This patent discloses the tagging of metal pins for mounted objects with light-activated micro-transponders; and provides an arrangement comprising a pin or a piece of jewelry and a transponder affixed thereto. The transponder can be a very small, light-triggered transponder.

U.S. Pat. No. 9,418,321 of Gruda et al. Issued on Aug. 16, 2016

This patent discloses a tissue carrier for the processing and storage of small tissue samples, such as the samples obtained in histopathology laboratories. Two main types of tissue carriers are the subject of the invention: tissue cassettes and glass slides.

Accordingly, the invention comprises a tissue cassette (a) configured to (i) retain therein a tissue specimen, (ii) have slots to allow externally applied reagents to act on the tissue specimen retained within the tissue cassette, and (iii) facilitate removal of the tissue specimen after chemical processing and (b) having plastic side walls;

a light-triggered, compact transponder chip embedded within one of the side walls and oriented to be triggered from the side of the tissue cassette; and a slotted form factor configured to align the tissue cassette so that a laser triggering signal aligns with the transponder as the cassette is slid in the slot—wherein said transponder chip the tissue cassette has at most only any embedding cavity as structure that is specifically adapted to receive said transponder, and wherein the compact transponder chip is embedded by heating it to a temperature above the melting point for the plastic and sinking it into the plastic, and wherein the embedding of the transponder chip preserves the structural integrity of the tissue cassette.

Gruda et al., "A System for Implanting Laboratory Mice with Light Activated Microtransponders", J. Am. Ass. Lab. Animal Sci. 49:6 (November) 2010

This publication describes a new radiofrequency identification tagging method that uses 500-μm, light-activated microtransponders implanted subcutaneously into the ear or tail of mice. The preferred location for implanting is in the side of the tail, because implantation at this site was simple to perform and was associated with shorter implantation times (average, 53 versus 325 s) and a higher success rate (98% versus 50%) compared with the ear. The main benefits of using light-activated microtransponders over other identification methods, including other radiofrequency identification tags, is their small size, which minimizes stress to the animals during implantation and low cost due to their one-piece (monolithic) design. In addition, the implantation procedure uses a custom-designed 21-gauge needle injector and does not require anesthetization of the mice.

Elva J. H. Robinson and Wlodek Mandecki, "Distributed Decisions: New Insights From Radio-Tagged Ants", In: Ant Colonies: Behavior in Insects, Nova Science Publishers, Inc. 2010

Live ant colonies are used as model systems for the study of self-organization; and the viewing of ants as laboratory test agents has led to many insights into the emergence of complex behaviors. New advances in radio-frequency identification (RFID) technology now allow the exploration of ant behaviour at the individual level, providing unprecedented insights into distributed decision-making.

D. A Realistic Appraisal of Current Surgical Inventory-Part Control Problems

Unfortunately, a series of well recognized problems have long existed and still currently remain today in efforts to maintain a proper identification and true accounting of surgical instruments and tools, medical devices and grafts, and specific component parts used during complex medical procedures.

For example, even keeping an accurate track of the medical devices and medications used during medical procedures has been one of the major concerns of healthcare facilities for many years. The diversity and scale of these problems is particularly costly in many ways for large sized hospitals (having scores of operating rooms); and in the loss of millions of dollars for lost or displaced medical device inventory. The range and variety of errors which occur daily in the dispensing, administration and prescribing of medications and medical treatments have collectively and cumulatively resulted in an unacceptably large number of adverse patient reactions—including many deaths and permanent impairments—which in turn invariably then leads to ever-higher medical insurance costs and ever-more expensive legal judgments for medical malpractice.

Additionally, it is commonly recognized by hospital staff administrators that many different kinds of medical devices and articles often may become misplaced or lost during their travels from a central supply source to the various surgical units and departments, and/or to different sterilization process areas, and/or to alternative operating rooms and surgical operating practices. Moreover, even when the medical device is brought into the correct and appropriate medical treatment area, the actual use of the medical device by surgeons within that specific medical treatment area for a particular patient is quite often not tracked, nor recorded, nor even recalled. Consequently, many types and kinds of implanted medical devices go untracked and unaccounted for in the patient's medical/surgical history, as well as in the medical facility's in-house billing practices.

Furthermore, it is common practice today to employ "renegade" medical devices—such as those items brought into an operating room by a sales representative from a medical device supplier company. These "renegade" medical devices are routinely utilized for the patient's benefit; and become surgically implanted into a patient with no written mention nor any official recordation of the now-engrafted "renegade" device ever having been in the specific operating room, or even being present within the medical facility. Worse yet, if there is a subsequent FDA recall of the "renegade" medical device, it is almost impossible at that later date to recall and identify which particular patient did in fact actually receive the "renegade" medical device, owing to the huge informational gap in the official record-keeping.

SUMMARY OF THE INVENTION

The present invention is a parts-inventory control system for tracking the use of and accounting for the ultimate disposition of at least some of the component parts needed for engrafting a complete implant as that component part of is separately surgically introduced in-vivo at a preselected anatomic site upon or within the body of a living subject. The parts-inventory control system thus comprises:

(1) a prepared-in-advance, inventory-parts dual correlation whereby a 1st correlation links each component part of the complete implant with a corresponding component part identification number, and wherein the 2nd correlation links each of said component part identification numbers with a corresponding singular RF signal;

(2) a preformed, sterilizable on-demand, modular kit housing at least some of the component parts needed for engrafting a complete implant which is to be surgically introduced in-vivo upon or within the body of a living subject, wherein said modular kit has set dimensions, a fixed configuration, a discernible face surface, and a plurality of shaped wells suitable for individually housing said component parts;

(3) a plurality of discrete use-tracking badges individually suitable for affixation at a pre-selected location on a face surface of said modular kit, wherein each of said use-tracking badges corresponds to a unique component part identification number and is able to release a corresponding singular RF signal on-demand into the ambient environment, and wherein each of said use-tracking badges is comprised of (α) a discernible foundation layer having set dimensions, a fixed configuration, and an exposed face surface, said foundation layer being formed of at least one and not more than three different preformed sheets joined together in overlay series, each of said preformed sheet being selected from the group consisting of a flat backing sheet composed of a dense and visibly colored matter, a planar sheet composed of durable and visibly clear light transparent material, and a numbered label indicative of one specific component part of said complete implant, (β) an operative, micron-sized, photovoltaic cell-chip transponder unit disposed upon and contained within the surface area of said foundation layer, said photovoltaic cell-chip transponder unit becoming activated and energized by light energy to generate and electronically emit a singular RF response signal indicative of a specific component part number into the ambient environment, and (γ) a preformed planar top sheet disposed upon and adhered fluid-tight to said photovoltaic cell-chip transponder unit and the face surface of said foundation layer;

(4) at least one discernible modality disposition-accounting assembly suitable for on-demand affixation at a preselected location within the spatial confines of the operating room, wherein said modality disposition-accounting assembly presents an array of not less than two and not more than six transaction mode subassembly units and wherein each of said subassembly units in said array is spaced apart from the others in sequential series, said modality disposition-accounting assembly comprising (α) an optionally present, preformed planar base sheet composed of a durable and visibly clear light transparent matter, wherein said optionally present planar base sheet has a set elongated configuration and predetermined millimeter-sized length, width, and thickness dimensions, presents a discrete anterior face surface and a discrete posterior face surface, and has a visibly clear adhesive coating disposed upon its posterior face surface, (β) a plurality of preformed flat backing sheets which are each oriented and aligned, spaced apart, and positioned in sequential series, wherein each of said intermediate backing sheets is composed of a recognizably different and visually distinguishable colored material, and wherein each of said colored intermediate backing sheets has a pre-selected configuration and thickness dimension, presents limited length and width millimeter-sized dimensions, and has an anterior face surface and a posterior face surface of predetermined surface area, (γ) one discrete operative micron-sized photovoltaic cell-chip transponder units disposed upon and contained entirely within the anterior face surface area for each of said colored backing sheets, wherein each of said photovoltaic cell-chip transponder units is separately activated and individually energized by light energy to generate and electronically emit one singular RF response signal into the ambient environment, and (δ) a preformed planar top sheet disposed upon and joined fluid-tight to each of said operative micron-sized photovoltaic cell-chip transponder units and to said anterior face surface area of each of said colored backing sheets, wherein said planar top sheet is composed entirely of a durable, visibly clear, transparent material, presents a discrete anterior face sheet surface and a discrete posterior face sheet surface, has an elongated configuration and millimeter-sized length and width dimensions which are not less than the dimension of said colored backing sheets, has a visibly clear, light transparent adhesive coating disposed upon its posterior face surface;

(5) a preformed, light-energy emitting on-demand, wand which generates a photon stream, has a fixed light beam diameter size, and emits light at a prechosen wavelength and at a pre-determined intensity;

(6) a telemetric RF signal receiver able to receive and then convey a range of different and diverse RF response signals after said RF signals are generated and released into the ambient environment; and (7) at least one RF signal compilation unit in communication with said RF signal receiver, wherein said RF signal compilation unit accepts, accumulates and records all conveyed RF response signals as data, compiles and analyzes the conveyed RF signal data, and is able to display the conveyed RF signal data in at least one visual format.

BRIEF DESCRIPTION OF THE DRAWING

The present invention may be more easily understood and better appreciated when taken in conjunction with the accompanying Drawing, in which:

Prior Art FIG. 1 presents Table A, which is an illustrative and representative listing of conventionally known and used implants and complete implant constructs;

Figure 2A:
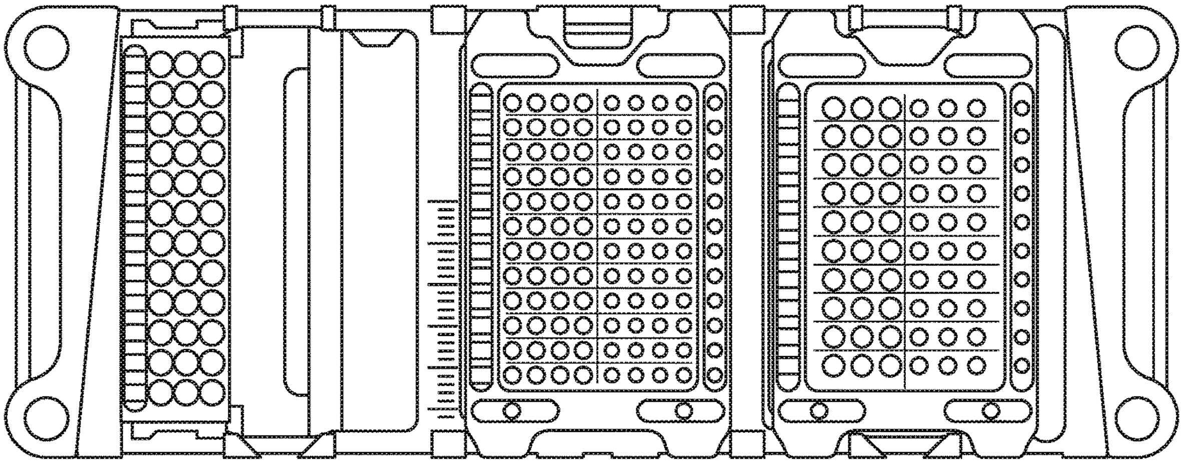
Figure 2B:
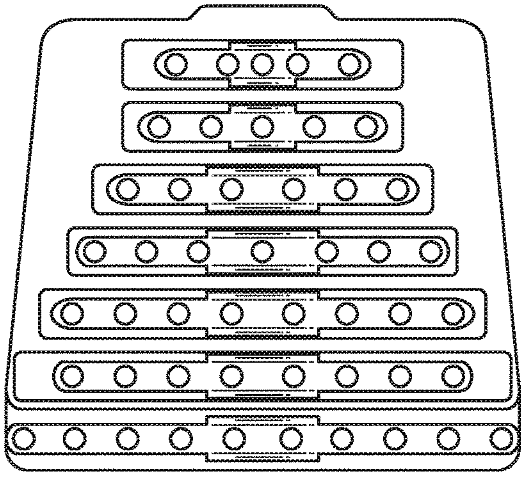
Figure 3:
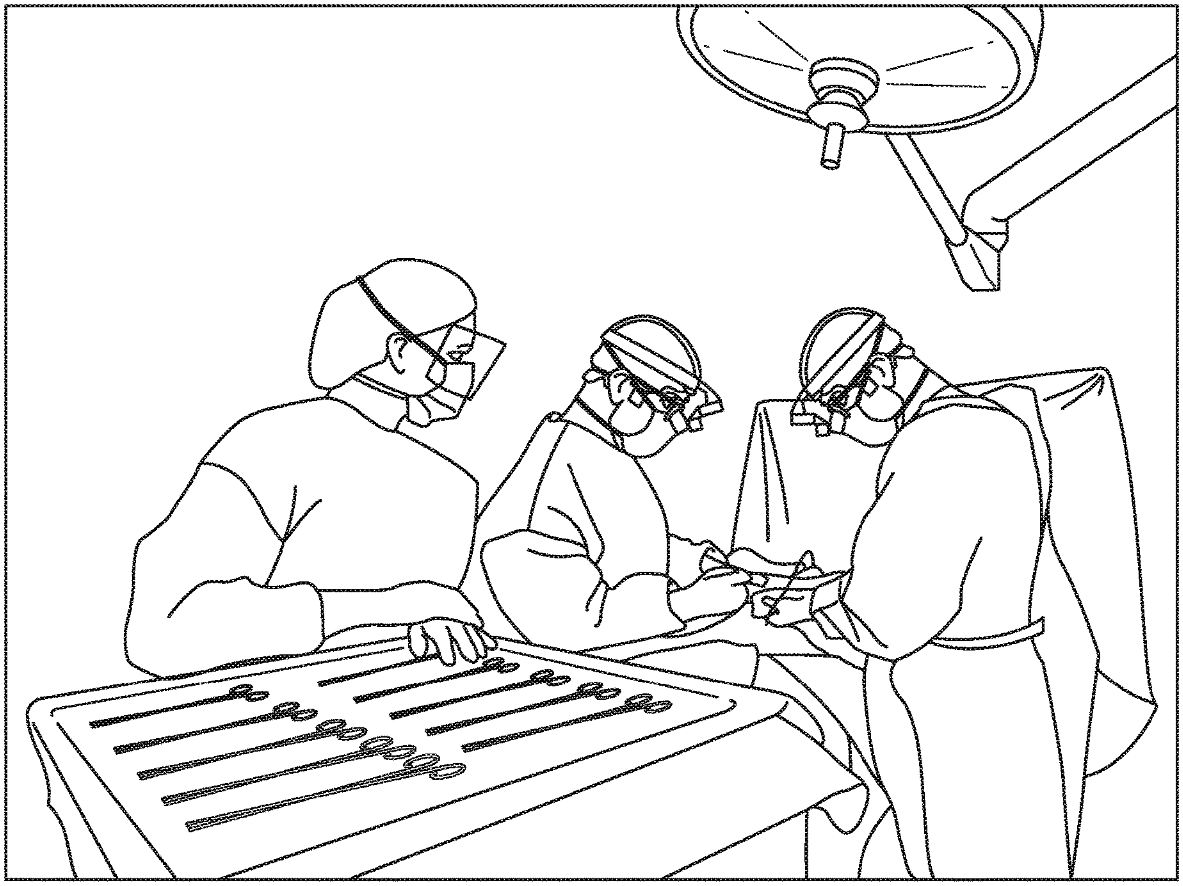
Figure 5:
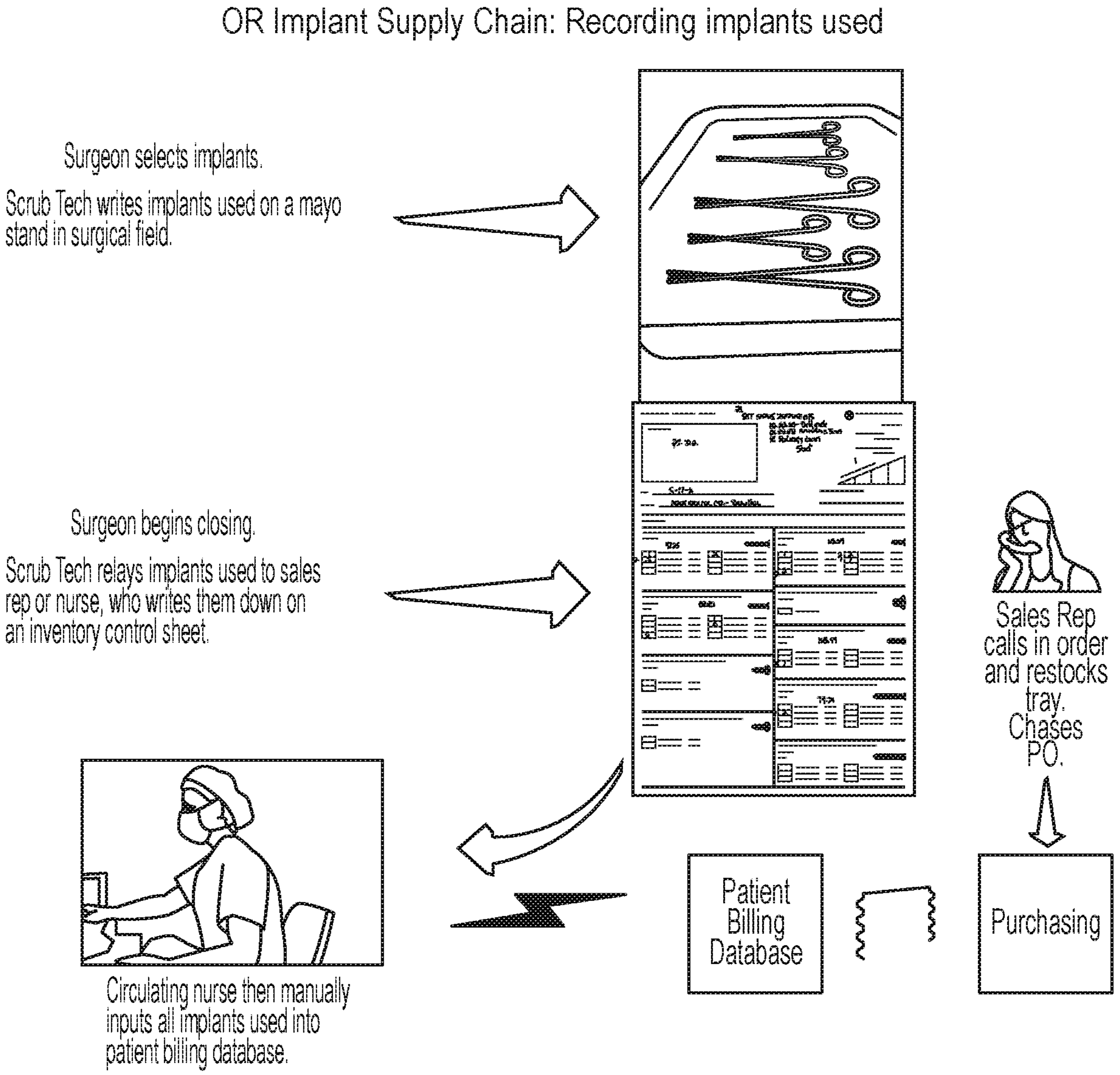
Figure 6:
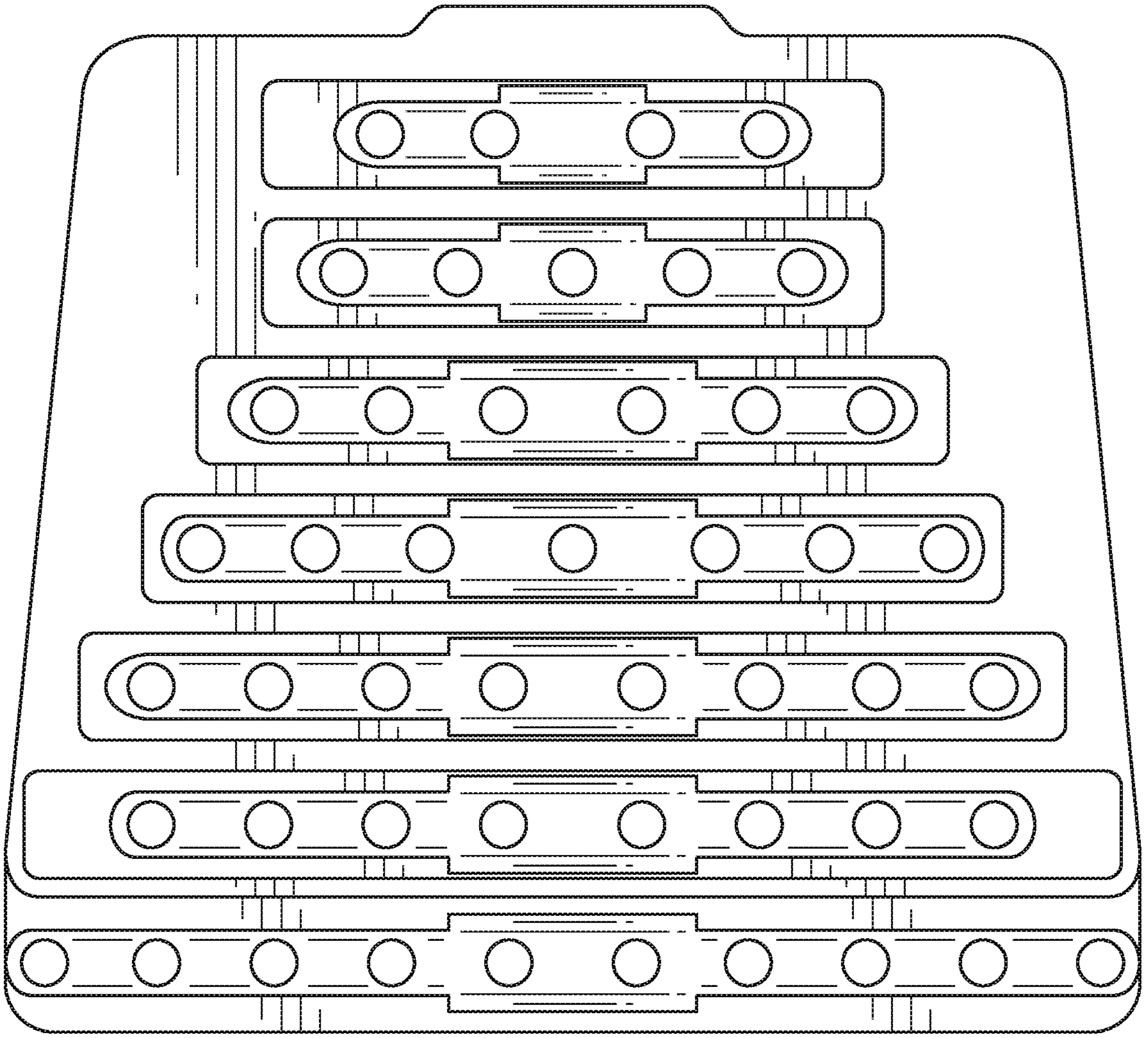
Figure 7:
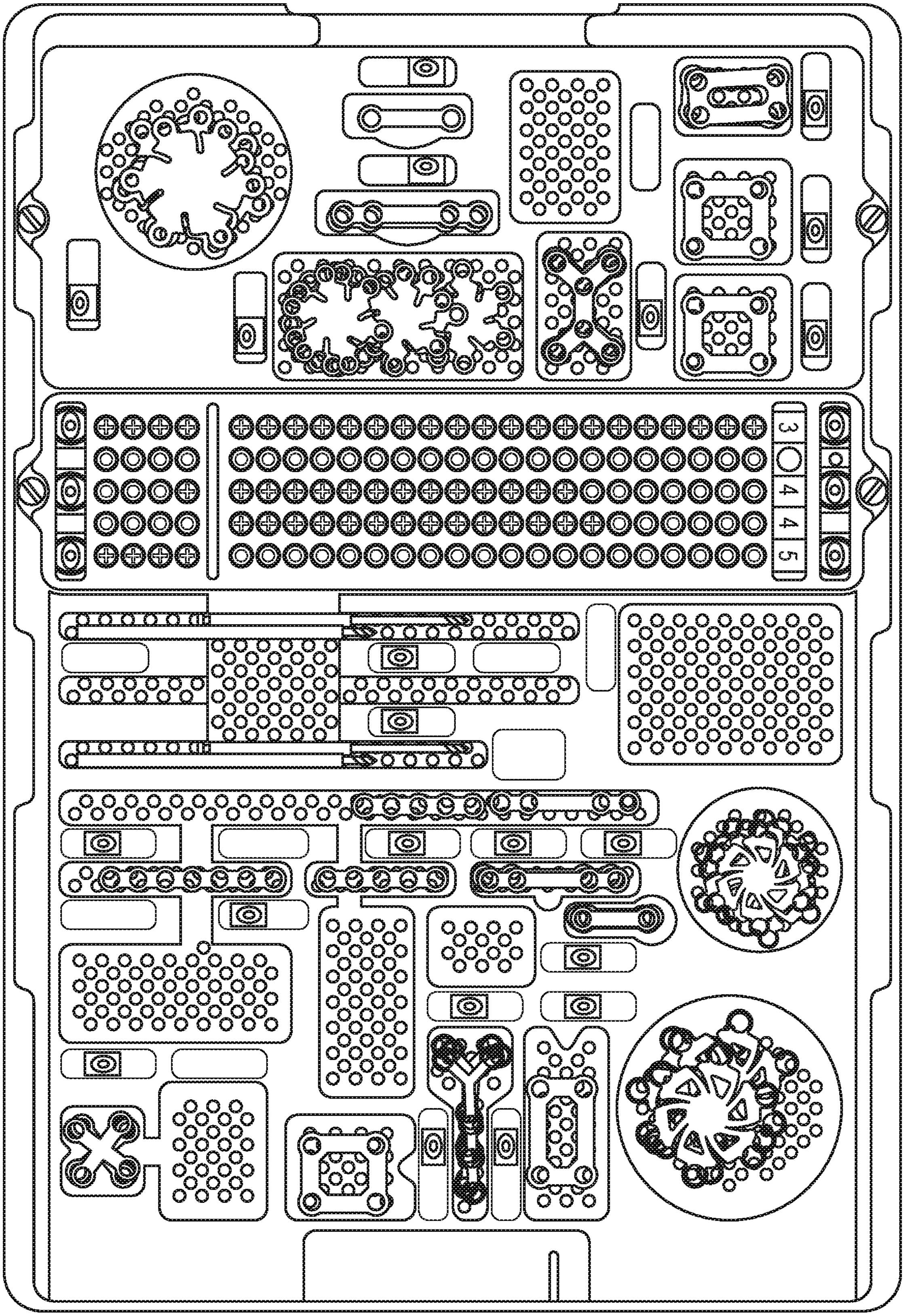
Figure 8A:
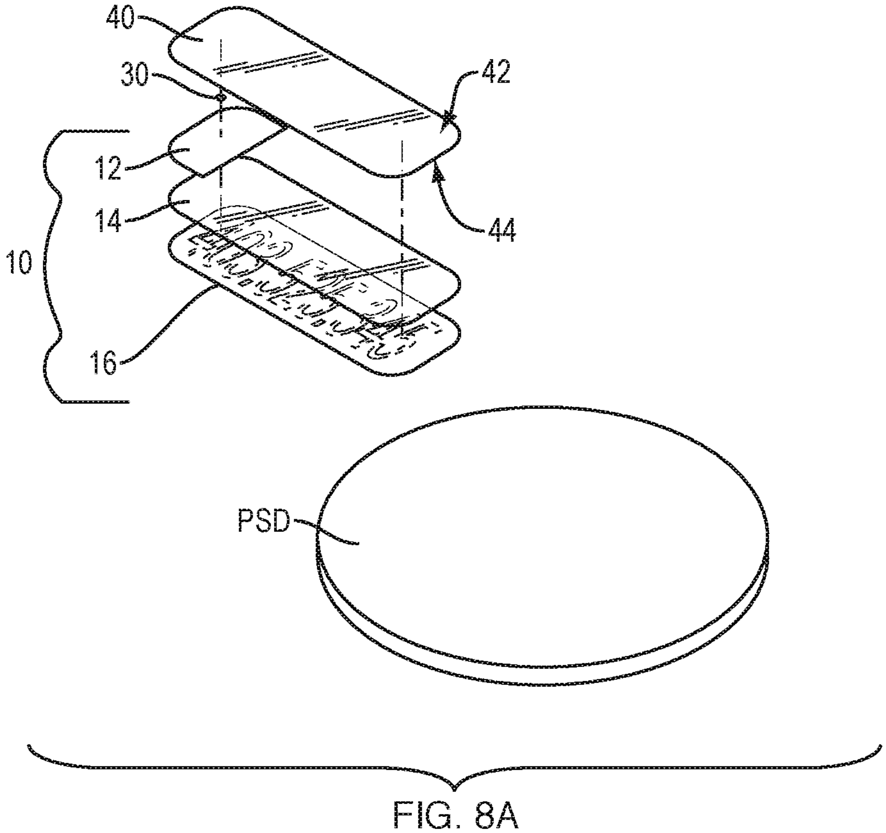
Figure 8B:
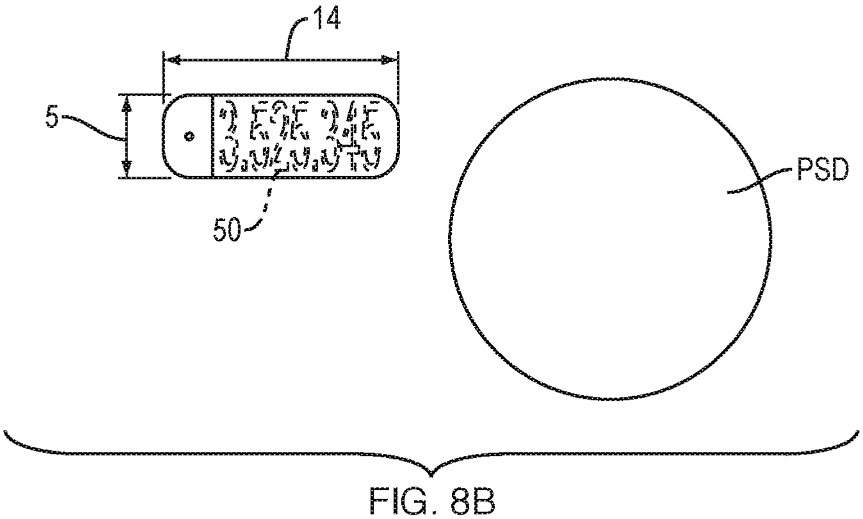
Figure 9A:
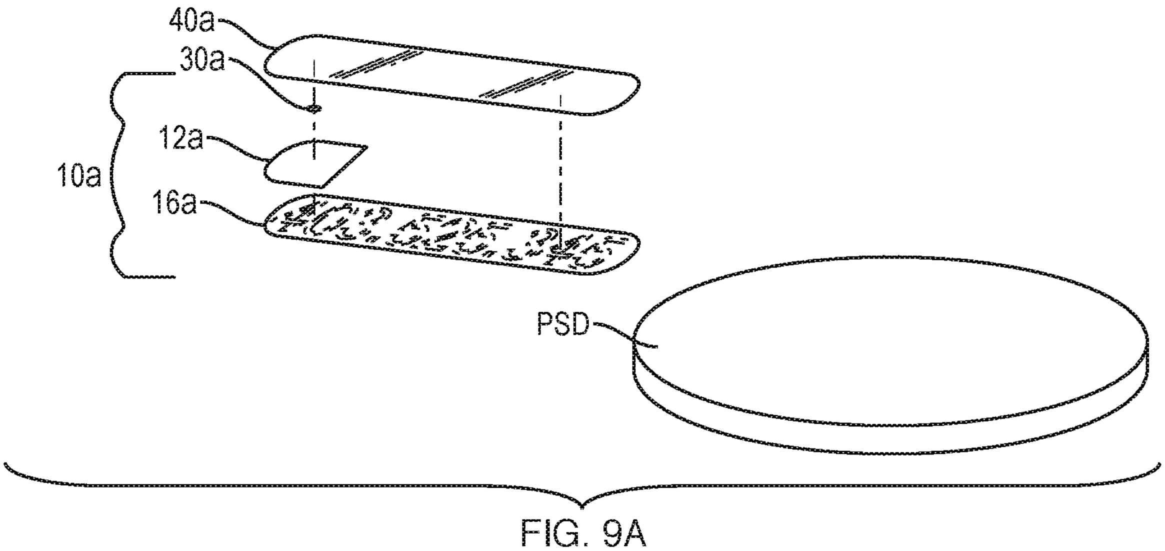
Figure 9B:
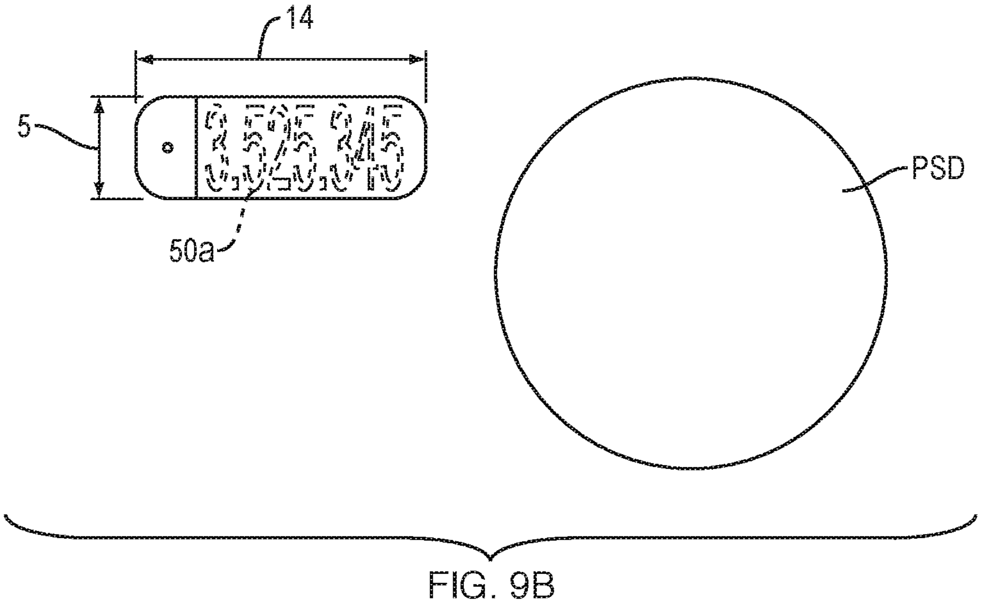
Figure 10A:
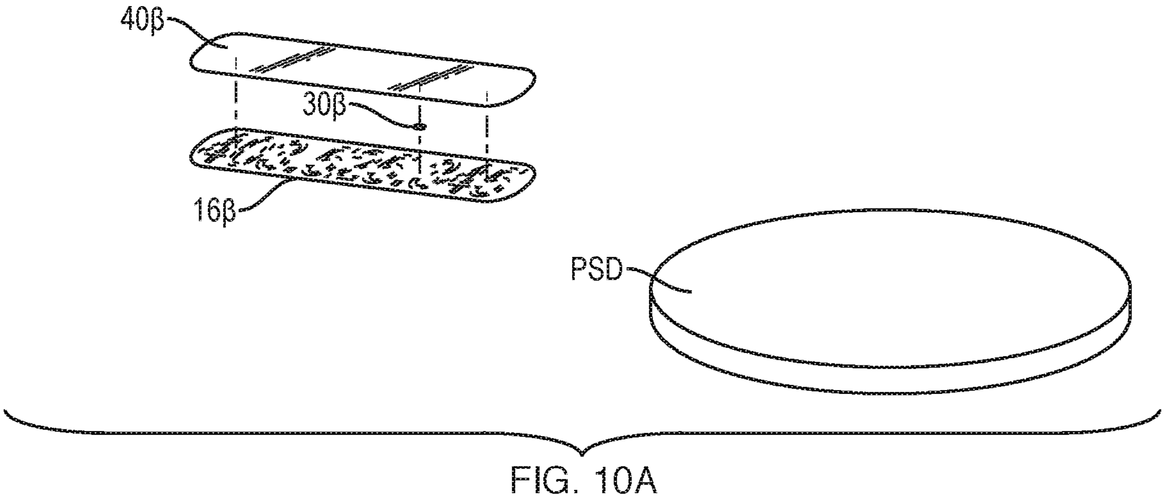
Figure 10B:
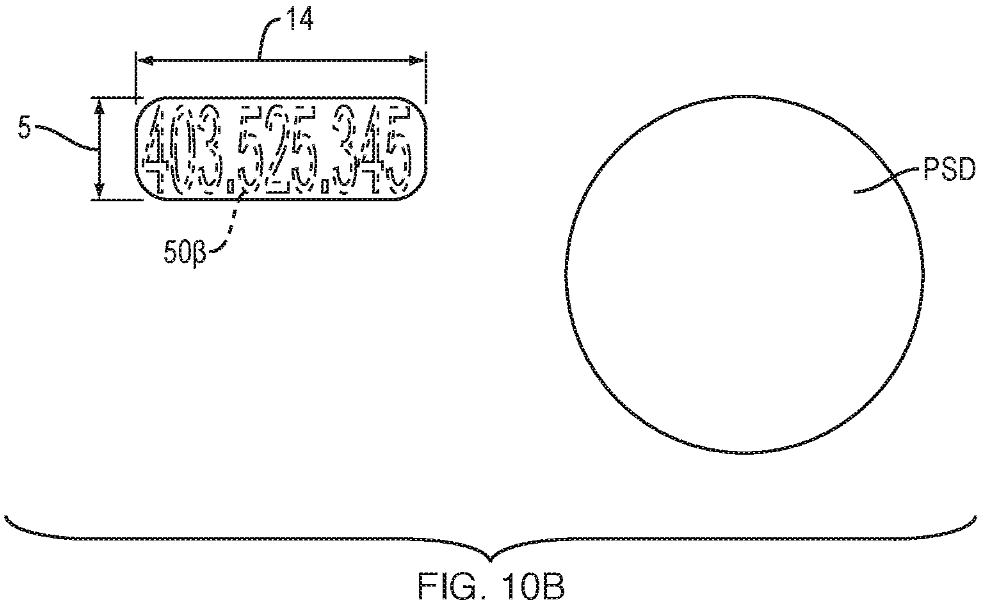
Figure 11:
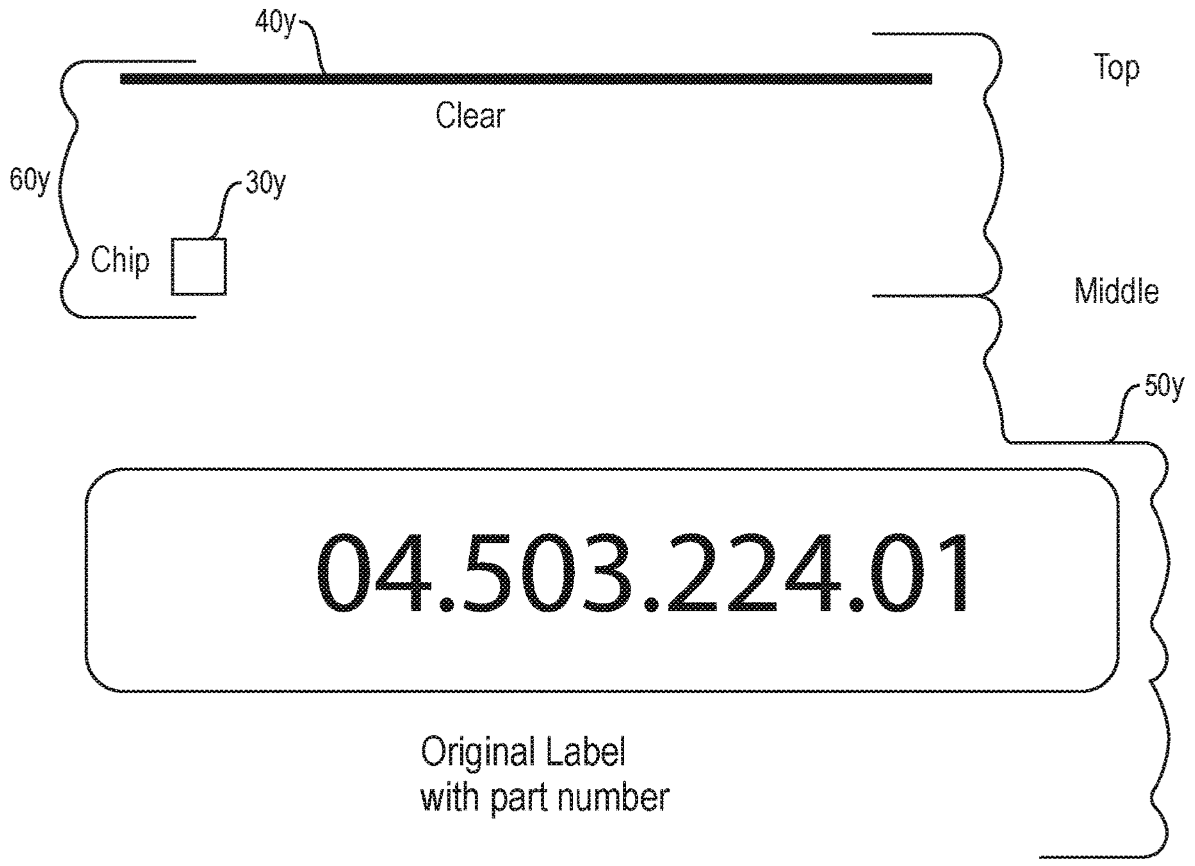
Figure 12A:
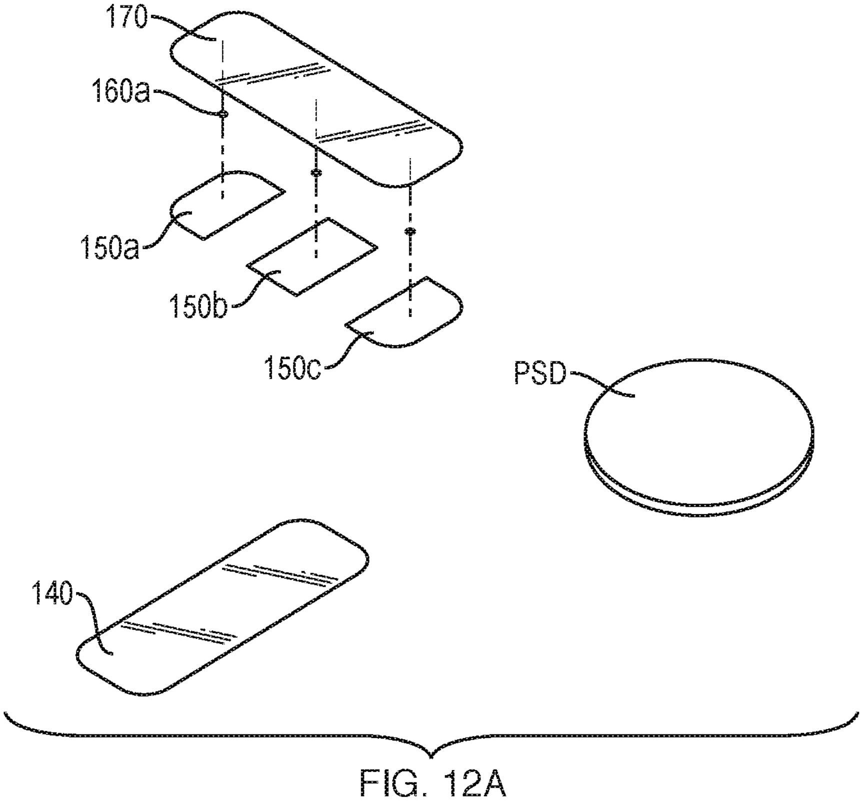
Figure 12B:
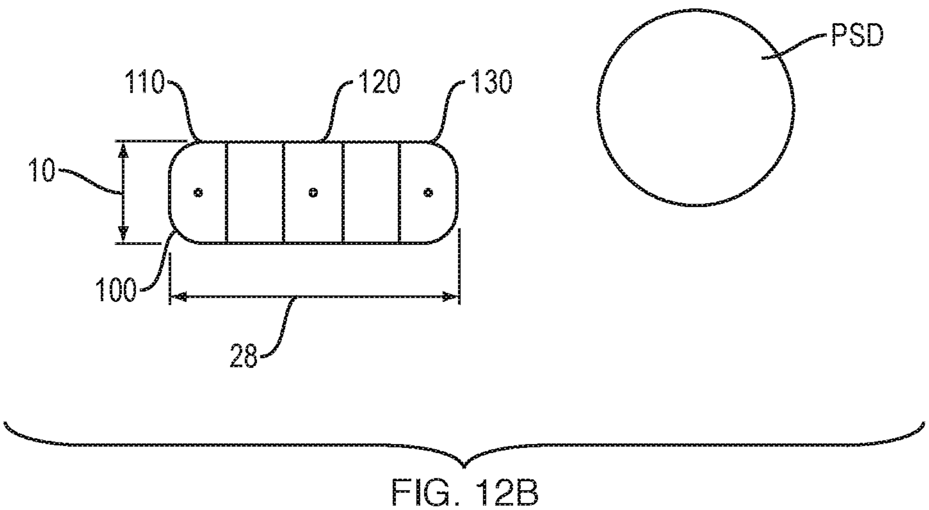
Figure 13:
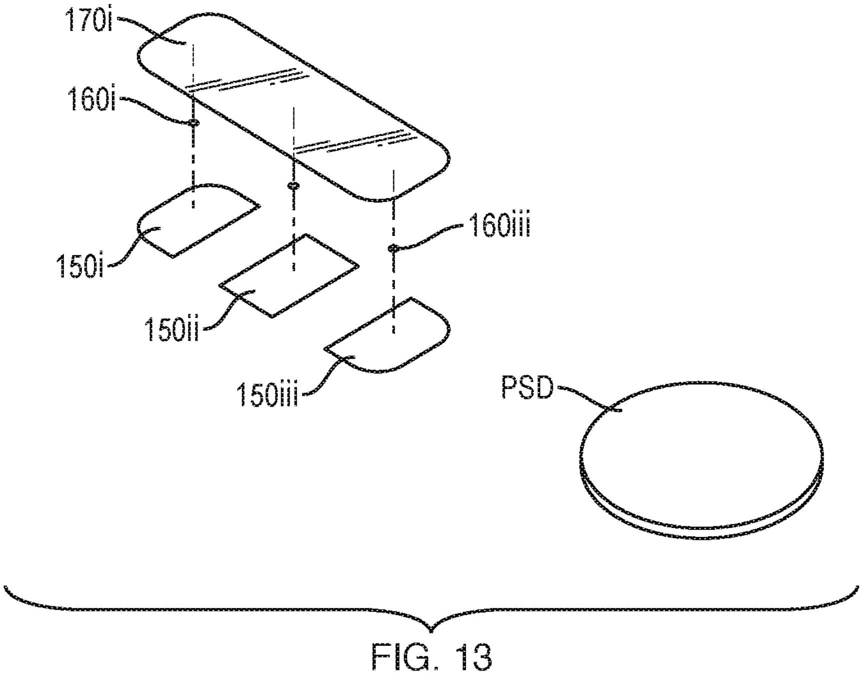
Figure 14:
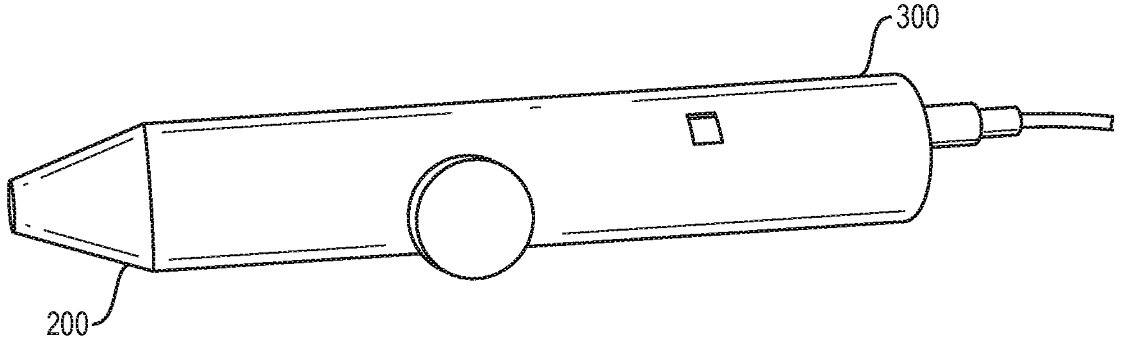

Prior Art FIGS. 2A and 2B respectively are photographs illustrating a typical format and representative example of a sterilized modular kit housing some of the component parts required for engrafting a complete implant construct in-vivo;

Prior Art FIG. 3 is a photographic illustration of the surgeon(s) working with a surgical technologist, who is also dressed in sterile garb and stands in the aseptic operating field with the surgeon;

Prior Art FIG. 4 is an illustrative example of a pre-printed form traditionally called an "Inventory Control Sheet", which conventionally is used to organize the recorded random information that the surgical technologist has previously written down on a mayo stand;

Prior Art FIG. 5 is a flow chart which summarizes the entire conventional practice and surgical procedure for implants and complete implant constructs as a whole;

Prior Art FIG. 6 is a magnified illustration of FIG. 2A above which shows a plurality of original component part number labels;

FIG. 7 is a representative and illustrative example of the present invention which shows the manner by which many use-tracking badges can be affixed at individual site locations on the exposed face surface of a modular kit;

FIGS. 8A and 8B respectively are illustrations showing a preferred embodiment of the use-tracking badge in exploded and fully erected views, as well as in size relationship to a penny sized disc ("PSD");

FIGS. 9A and 9B respectively are illustrations of Format Variant A as a whole, wherein this variant of the use-tracking badge appears in complete and exploded views, and in size relationship to a penny sized disc ("PSD");

FIGS. 10A and 10B respectively are illustrations of Format Variant B as a whole, wherein this variant of the use-tracking badge appears in complete and exploded views, and in size relationship to a penny sized disc ("PSD");

FIG. 11 is an illustration of the intended manner of in-situ use-tracking badge generation and shows an exploded view of the Precursor Construct T kludge as an antecedent article of manufacture and a forerunner product formed by a preformed, planar top sheet and a single operative, micron-sized, photovoltaic cell-chip transponder unit;

FIGS. 12A and 12B respectively are illustrations of a preferred modality disposition-accounting assembly, which presents an array of three discernible mode disposition subassemblies together with a penny-sized disc (or "PSD") for making size comparisons visually;

FIG. 13 is an illustration of a variant format of the modality disposition-accounting assembly which presents an array of three discernible mode disposition subassembly when the preformed planar base sheet is not present; and FIG. 14 is a photographic illustration of a preferred and commercially sold light-emitting wand embodiment, which is capable of energizing and then receiving the RF response signal released by individual micron-sized photovoltaic cell-chip transponders.

DETAILED DESCRIPTION OF THE PRESENT INVENTION

I. The Substantive Problems Solved by the Present Invention

In order to appreciate properly what are the unique features and many advantages of the present invention as a whole, one must see the nature of the true problems from the perspective and frame of reference of the surgical operating team and the medical facility's administrative surgical staff.

For the surgical team performing an in-vivo implant grafting procedure, there are a number of serious and substantive challenges which must be individually confronted and solved. All of these are manifest problems; and each of them must be effectively addressed and solved. In addition, the entire set of challenges must be successfully answered in decisive terms. Consequently, what might to the unacquainted seem to be merely superficial considerations or cursory questions—upon subsequent reflection and deliberation instead reveals itself to be truly substantive, significant, and of medical value.

The true perspectives and proper reference context concerning these major problems therefore include all of the following:

(a) A first medical challenge is to provide an operating room situated inventory-parts control system and arrangement that is both facile, dependable, and fully responsive to the surgeon's particular needs when engrafting an implant in-vivo. The necessary effort includes the capability to track and account for an enormous variety of different inventories, each of these inventories constituting the requisite type and number of individual component parts needed for one particular complete implant; and on each engraft occasion, the capability to identify accurately and record precisely the use and disposition of each individual component part actually used by the surgeon when joining the complete implant upon or into the body of the living patient.

(b) A second medical problem is: How does one obtain an operating room situated inventory-parts control system and arrangement which will function indefinitely and can be used reliably and repeatedly for at least several calendar years' time.

(c) A third major medical difficulty is the availability of an operating room situated inventory-parts control system and arrangement which allows for and is able to accommodate the huge variety of in-vivo engraftable implants and implant constructs—given that no two implant types are alike as to their structural parts, or its intended anatomic purpose, or the true number of requisite parts, or the nature of its particular component parts.

(d) A fourth medical burden is: How does one provide for the broadcast and detection of individual RF signals in a system and arrangement where multiple CMOS-chip transponders exist as operative components. This particular challenge presents two notably different, but intimately related, problems, which are these:

- To be both operative and effective, there must exist an unobstructed and optically clear travel direction pathway for an activation signal to reach the embedded CMOS-chip. This unhampered travel direction pathway requirement exists and signifies that any prechosen type of activation signal and energy source (such as laser light energy) sent by a remote transceiver device must not only have unhampered access to and an open path for directly reaching the embedded CMOS-chip of the transponder unit; but also present sufficient signal strength and energy power at the moment of direct contact to activate the CMOS-chip and allow the then energized chip to respond and broadcast its unique recognition-return signal to a remotely placed reception device.
- The mode of attachment for the discrete CMOS-chip must avoid unintentional creation of obstructions and avert accidental blockage of an available clear optical pathway to the CMOS-chip. Thus, the affixation technique for the CMOS-chip cannot allow use of any dense adhesive label which might be wound over itself, thereby unintentionally covering the CMOS-chip, and consequently not allowing the CMOS-chip to receive sufficient activation signal and/or energy power to activate or to broadcast a response signal in sufficient strength and adequate distance for the remote receiving device to record it.

II. Unexpected Advantages and Unforeseen Benefits

A significant number of unexpected advantages and unforeseen benefits are provided by the inventory-parts control system and supervisory arrangement of the present invention. The capabilities stated below explicitly set forth some of the most valued characteristics and features of the invention as claimed.

In this regard, one should now recall and reconsider what the conventional surgical practice and procedure has traditionally been to date—as summarily described above and as illustrated by the flow chart of Prior Art FIG. 5. In this context also, it is emphasized here that the information given below is not merely a pro forma listing of certain traits and attributes; but rather is a statement which provides a true explanation and an accurate understanding of the meaningful advantages and particular benefits that are in fact provided by the present invention, as seen from the viewpoint and perspective of the ordinarily skilled practitioner working today in the implant medical/surgical field. Accordingly, these qualities include all of the following:

1. The control system of the present invention carefully monitors and fully accounts for some or all the available component parts that may be—but are not necessarily always—actually used in-vivo to engraft a complete implant onto or within the body of the patient. Thus, regardless of the number of parts constituting the complete implant, the control system can and will identify each component part individually; and in detail accurately indicate what the ultimate disposition and present status of that single component part is.

2. The control system of the present invention tracks each component part of the complete implant via its correlated and corresponding part number identification; and will concurrently release one singular and unique RF signal into the environment as a broadcast RF identifying tag indicative of that specific component part.

3. Due to the nature of the relationship between the laser light energy which powers the micron-sized photovoltaic cell-chip transponder unit as well as because of the small size of the chip transponder unit itself, the control system of the present invention can identify and distinguish between different implant parts in the tray that are in very close proximity with great accuracy, and with little chance of "misreading" the wrong chip transponder unit 4. The control system of the present invention can and will automatically receive, record, and store a large variety of different broadcast RF signals concurrently, in a manner which indicates what the actual use and ultimate disposition for each specific component part was during the performance of the surgery.

5. The control system of the present invention envisions and provides for the accumulation, compilation, and analysis of one, or some, or many, or even all of the individual component parts which were actually used by the surgeon during the engrafting procedure.

6. The control system of the present invention provides a comprehensive inventory of parts statement and a listing of each component part actually inserted into the body of the patient as a recorded set of individual component part numbers on-demand; and offers a recorded listing which, in turn, informs the surgical technician of what specific component parts then need to be replenished, when the tray is re-stocked post surgery.

7. The control system of the present invention substantively reduces the risks of human error when accounting for each of the component parts that were actually used in the surgery; and distinguishes those parts actually grafted into the patient from those other component parts which were either returned to the available inventory or were discarded as surgical waste.

8. The unique nature of the variants in the control system envisions and purposely allows for the retrofitting of existing modular kits and trays presently having one or more pre-existing original component part number identification labels affixed to the face surface of the kit or tray.

9. The control system of the present invention has the distinct advantage of using a micron-sized photovoltaic cell-chip transponder unit having extreme durability despite being repeatedly subjected to water and other aqueous fluids; and to cleaning agents and other noxious chemical compositions; and to harsh sterilization environments. In particular, the present control system works far better than small 2D barcodes, which fade with repeated washes and quickly lose contrast and readability.

III. The Control System & Supervisory Arrangement as a Whole

The present invention is an inventory-parts control system and supervisory arrangement for tracking the actual use of and for accounting the ultimate disposition of at least some of the individual parts constituting a complete implant. The system is fully operative and functional for inventory control purposes throughout the entire surgical procedure; and will track and account for a component item of that implant as it is individually introduced and engrafted in-vivo at a preselected anatomic site upon or within the body of a living subject.

In order to achieve these goals, the inventory-parts control system and supervisory arrangement of the present invention employs not less than seven (7) essential elements, which are cumulatively and collectively as follows.

Arrangement Requirement 1: An Inventory-Parts Dual Correlation

The present invention is based upon a double correlation system and employs a tandem reciprocal correspondence of information, which are: A $1^{st}$ correlation made between each implant component part and a single and an unique corresponding part identification number; and a $2^{nd}$ correlation made between a single component part identification number and an identifying and directly corresponding singular RF signal.

Ж For the $1^{st}$ correlation, each requisite component part constituting the complete implant must be given, must be associated with, and must be uniquely recognizable by a single corresponding component part identification number—as an organized and systematized 1:1 reciprocal correlation. The existence of such a prepared in advance $1^{st}$ correlation is an unequivocal and absolute requirement; and once made, should be a permanent arrangement and constant reciprocal correspondence.

The underlying reason and rational for this correlation demand is this: Because each type and kind of implant is to be erected in-situ piece by piece upon or within the living body of the patient, each particular implant will invariably comprise at least one functional device, object or article; will require a range of different supports, plates, posts, girders, braces, rods, joices, or beams; and will use associated hardware—such as surgical nails, screws, bolts, pins, anchors, and K-wires—to tangibly attach and join the complete implant item in-vivo at a preselected anatomic site upon or within the body of a living subject.

The present inventory-parts control system expects that many of the devices, objects and articles that are used in the erection and formation of the complete implant in-situ, as well as such hardware pieces which might at any time be employed by the surgeon to join and physically attach the implant to the body of the patient—will have its own unique and individual component part number identification. As merely a simple representative example: A 4 mm long Philips screw, and a 5 mm long Philips screw, and a 6 mm Philips screw, will each have its own singular and individual component part number; and each such identifying part number will effectively separate and meaningfully distinguish one sized screw from each of the two other screw length sizes.

In addition, one should recognize that in limited stances, such individual component part identification numbers not only already exist, but also often visibly appear as original number labels which are then tangibly adhered to the exposed surface of the modular kit. These adhered original number labels typically are the manufacturer's or vendor's own prepared numbered listing for those items, supplies and associated hardware needed for erecting and engrafting the complete implant in-vivo. To illustrate this situation, particular attention is directed to FIG. 6 (an enlargement of FIG. 2B), which shows many different original number part labels visibly located on the exposed exterior surface of the modular kit adjacent to each of the support arms then housed within the shaped wells of the modular kit.

Consequently, the present invention presents an explicit and absolute demand for a 1st reciprocal correlation: Each operative item, and every functional component, and all the tangible hardware support and attachment/juncture pieces—without regard to the individual size, shape, and dimensions—must be assigned and be directly correlatable with its own uniquely recognizable and identifying component part number.

Ж To meet and satisfy the requirement for a $2^{nd}$ reciprocal correlation, a prepared-in-advance correspondence is made between each uniquely recognizable component part number identification and one singular directly associated RF signal.

Again, as merely a simple representative example: A 4 mm long Philips screw, and a 5 mm long Philips screw, and a 6 mm Philips screw are similar except for its length dimension. Thus, each individual length Philips screw will have its own uniquely associated and corresponding singular RF signal; and each of the three different RF signals is a singular identifying electronic emission which will separate and distinguish one particular screw length size from both of the two other RF signals indicative of the other screw length sizes.

This $2^{nd}$ correlation and correspondence is also a direct 1:1 relationship. Each singular RF signal is one that can be detected, received, and recorded by a RF signal receiver; and is a RF signal which then can be stored indefinitely within the electronic memory of a RF signal data compilation unit. Consequently, the existence and use of such a prepared in advance $2^{nd}$ correlation is an unequivocal and absolute requirement which will appear and be employed in combination with the 1st reciprocal correlation.

Arrangement Requirement 2: At Least One Preformed, Sterilizable On-Demand, Modular Kit Housing Individual Parts)

Ж Accurately keeping track of the of the actual use and true ultimate disposition of the individual component parts needed in-situ to construct and attach the chosen implant in-vivo via the surgical procedure is both medically crucial and essential for both the surgeon and the patient. This criticality and urgency stems from several different but related causes:

First, the surgeon must have intimate knowledge and precise awareness of what tangible implant parts have in fact been surgically inserted into and tangibly joined to living body at all times during and throughout the entire surgical procedure. It is medically vital and essential that no unattached hardware or structural parts be left accidently and unknowingly in the living body at any time during the surgical grafting process.

Second, the patient's surgical record must accurately reflect and document precisely what items have actually been surgically put into and joined to the body of the patient; and to be able to separate and distinguish those component parts actually in the body from those individual pieces which have (for any reason) been removed and replaced back into the modular kit; or alternatively have been deemed unusable (for any reason) and thus were discarded as medical waste.

Third, the operating room surgical technologist or circulating nurse, and the hospital's administrative and billing staff must have a true track of and verifiable accounting for all the individual component pieces actually used at any time during the surgical implant process. This requirement and need pertains to the replenishing of inventory parts for the modular kit; and to the reordering and restocking of depleted implant parts; as well as for the proper billing of the attendant true surgery costs to the medical insurance carrier or financially responsible person for performing the implant surgery itself.)

Ж In order to meet and satisfy these surgical needs, a modular kit or tray housing is typically employed by the surgeon and surgical technologist to hold and contain at least some of the requisite component parts for a complete implant to be surgically engrafted in-vivo onto or within the body of a living subject. As shown by Prior Art FIGS. 2A and 2B respectively herein, at least one modular kit is typically prepared in advance which offers a modular kit box; presents a modular kit face surface; and has a plurality of shaped wells for housing and storing the various hardware component parts needed to engraft the complete implant in-vivo. Attention is also again directed to Prior Art FIG. 6 (an enlargement of Prior Art FIG. 2B) which shows many different part identification number labels located on the exposed exterior surface of the modular kit adjacent to the individual support arms then housed within the shaped wells of the modular kit.

Arrangement Requirement 3: A Plurality of Discrete Use-Tracking Badges

The supervisory arrangement of the present invention utilizes a plurality of discrete use-tracking badges, each such badge being suitable for affixation at an individually selected location on the exposed face surface of the sterilizable modular kit (then containing at least some of the requisite component parts of a complete surgical implant). Thus, the working rule and requirement of the present control system and supervisory arrangement is that one use-tracking badge is uniquely associated with and lies tangibly affixed adjacent to each individual component part that is housed within the modular kit.

Accordingly, one discrete use-tracking badge is specifically assigned to, is intimately associated with, and reciprocally corresponds to a single component part (having its own unique part number identification). Moreover, the individually different use-tracking badges deployed and tangibly appearing upon the exposed face surface of the modular kit will each vary directly and be in 1:1 correspondence with the true number of different components parts then housed within the shaped wells of the entire modular kit.

A representative and illustrative example of the manner by which many discrete use-tracking badges can be affixed at individual site locations on the exposed face surface of a sterilizable modular kit is shown by FIG. 7.

In the particular instance illustrated by FIG. 7, it will be noted and appreciated that the number of use-tracking badges total 28 units in all; and that each badge is separately and individually affixed at approximately the following locations: Adjacent to each of the variously shaped large support plates housed at the top of the kit; at the kit center where a plurality of 3 mm, 4 mm, and 5 mm sized Philips screws are separately housed; and at the kit bottom where smaller-sized support plates of varying configurations are housed. Typically therefore, the total number of separate and individual use-tracking badges deployed over and affixed to the face surface of a single modular kit can routinely approach 30, or 40, or even more discrete embodiments in all.

In addition, as exists at many of the use-tracking badge affixation locations shown by FIG. 7, a numbered label is visibly present; and each of these numbered labels indicates and states exactly what the corresponding component part number identification is for that specific part. In this illustrated instance also, the use-tracking badges individually affixed to each of these locations are overlay variant constructions; and are purposely sized to incorporate and protect each of these pre-existing component part number labels within the measurable dimensions of each badge as a whole.

A. The Elements In Each Use-Tracking Badge Construction

As illustrated in detail by FIGS. 8A and 8B respectively, a preferred embodiment of a use-tracking badge 50 appears in exploded and fully erected views, as well as in size relationship to a penny sized disc ("PSD"). In general, a use-tracking badge can have about a 2-20 millimeter (mm) length dimension; and can have about a 3-6 mm width dimension; and can present a thickness dimension ranging from about 4-20 mils. However, as shown by FIG. 8B, the particular dimensions for the preferred use-tracking badge 50 are a length of 14 mm, a width of 5 mm, and a thickness of about 12 mils.

Notably, each operative use-tracking badge—without regard to its specific construction format, existing design variant, and preferred style particulars—is comprised of not less than three requisite elements, which are as follows.

Element (α): A Discernible Foundation Layer

The foundation layer is formed of at least one and not more than three different preformed sheets joined together in overlay stacked series; wherein each said sheet is one selected from the group consisting of a flat backing sheet composed of a dense and visibly colored matter, a planar sheet composed of durable and visibly clear light transparent material, and a visually-readable numbered label whose given number identifies one specific component part of a complete surgical implant or engraftable prosthetic device.

The discernible foundation layer as a whole, which is formed of at least one and not more than three different preformed sheets of material joined together in overlay series, is a discrete stratum of matter which preferably:

presents a pre-selected overall configuration and has limited millimeter-sized length, width and thickness dimensions;

has an anterior face surface and a posterior face surface;

is repellent to water and other aqueous fluids;

is resistant to cleaning agents and other noxious chemical compositions;

is enduring of harsh sterilization environments; and has a transparent adhesive coating disposed upon its posterior face surface.

As shown in detail by the exploded view embodiment of FIG. 8A, the discernible foundation layer 10 is in this illustrated instance formed of three different and distinct preformed sheets—a flat backing sheet 12 composed of a dense and visibly colored matter; a planar sheet 14 composed of durable and visibly clear light transparent material; and a visually-readable numbered label 16. These three discrete sheets 12, 14, and 16 are joined together fluid-tight in overlay stacked series; and collectively present a unified stratum of matter having a substantially rectangular overall configuration.

Furthermore, the foundation layer 10 as a whole (and without regard to the actual number of preformed sheets) will always cumulatively present an anterior face surface as its obverse side, and a posterior face surface as its reverse side. Both the obverse side and the reverse side of the discernible foundation layer 10 have particular functions and applications.

Element (β): A Photovoltaic Cell-Chip Transponder Unit

£ As shown by FIG. 8A, an operative, micron-sized, photovoltaic cell-chip transponder unit 30 lies disposed upon and contained within the anterior face surface area of the foundation layer 10. This photovoltaic cell-chip transponder unit 30 becomes activated and energized by light energy; and then will generate and electronically emit an unique RF response signal into the ambient environment, wherein each unique emitted RF signal correlates with and corresponds to a single component part number identification.

The photovoltaic cell powered-integrated circuit transponder typically comprises a silica wafer semiconductor chip with internal circuitry sufficient to broadcast a unique identifying number or data; but is a miniature-sized transponder unit which does not employ either a battery or large-sized antennae.

Accordingly and as seen in FIG. 8A, the operative micron-sized photovoltaic cell-integrated chip transponder unit 30 lies embedded within and is completely contained between the planar top sheet 40 and the foundation layer 10. In this protected position and location, the embedded photovoltaic cell-integrated chip transponder unit 30 can be activated and energized by light energy photons on-demand. Then, after receiving and converting such a light energy transmission, the embedded transponder unit will produce and electronically emit an encoded singular RF response signal—which travels through the material thickness of the transparent top planar sheet 60 and is broadcast into the immediately surrounding environment. Once broadcast into the ambient atmosphere of the operating room, the uniquely encoded singular RF response signal can be detected and accepted by a RF signal receiver located nearby; and the received RF signal can subsequently be electronically conveyed, recorded in memory, and stored indefinitely by a RF signal data compilation apparatus.

£ In this particular kind of CMOS technology, the embedded transponder's internal circuitry employs one or more tiny photocells which accept and absorb light energy rays (transmitted from a remotely located external light source) in order to activate and electrically power the chip's circuitry. The transponder also includes a very small signal-transmitting antenna by which a responsive RF signal broadcast is sent into the ambient environment for detection and acceptance by a remotely located reader/transceiver.

Operationally, each embedded photovoltaic cell-integrated chip transponder unit 30 (as appearing in FIG. 8 as a whole) will contain encoded identity information which relates to and identifies a single implant component and an unique identification part number. The photovoltaic cell transponder unit can receive and accept light energy photons from a light-emitting source; and can convert the received light energy into internal electric current power for the chip circuitry, which then holds encoded data indicating the identity number of the component part. The chip circuitry, in turn, then can produce and emit a singular RF response signal(s) corresponding to the transponder's individual coded numbered part identity data; and this emitted response RF signal is broadcast over a short distance into the surrounding ambient environment of the operating room.

After the response RF signal broadcast by the transponder unit 30 is detected and received by a RF signal receiver unit, an adjacently located computer controlled reader/transceiver unit decodes the response RF signal(s), stores the signal data in its memory, and typically displays the decoded specific component part identification number to the surgical technologist or technician.

£ The photovoltaic cell-integrated circuit transponder unit 30 embedded in the preferred use-tracking badge 50 is miniscule in scale and size; and is at most about 500 microns square in area, and typically is no more than about 100 microns in thickness or depth. Such micron-sized transponders with photovoltaic cell activated integrated circuitry are presently commercially manufactured and sold as the P-Chip® transponder [Pharmaseq Inc., Princeton N.J.].

The heart of the micron-sized photovoltaic cell-integrated chip transponder is an ultra-small light-powered electronic chip circuitry electrically joined to an antenna. The chip is a monolithic integrated electrical circuit made using standard/conventional manufacturing technology. An essential part of the P-Chip® transponder unit is its internal photovoltaic cell, which when illuminated by light energy, is activated and provides adequate electric power for operating the electronic circuits of the chip. The remaining electronic circuitry of the P-Chip® silicon wafer are typically a read-only memory unit for the unique 50-bit ID decoders and counters; and a small simple radio antenna for transmission of a return RF signal.

Moreover, there are commercially available at least two different micron-sized constructed versions of a completely functional and operative P-Chip® transponder: A 500×500×100 micron sized unit and a 250×250×50 micron sized unit respectively.

Element (γ): A Preformed Planar Top Sheet

₪ As shown by the preferred embodiment of FIG. 8A, a single preformed, planar top sheet 40 lies disposed upon and adhered fluid-tight to the photovoltaic cell-chip transponder unit 30 and the anterior face surface of the foundation layer 10. This planar top sheet 40 has certain properties and characteristics, which most desirably include:

- being composed of durable and visibly clear light transparent material;
- presenting an anterior face sheet surface and a posterior face sheet surface;
- having an elongated configuration and millimeter-sized dimensions which are not less than the size dimensions of the foundation layer;
- being repellent to water and other aqueous fluids;
- being resistant to cleaning agents and other noxious chemical compositions;
- being enduring of and resistant to harsh sterilization environments; and
- having a visibly clear adhesive coating disposed upon its posterior face sheet surface.

₪ It will be noted that the planar top sheet 40 must be composed of a clear material or visibly transparent substance which is repellent to water and other aqueous fluids; is resistant to cleaning agents and other noxious chemical compositions; and is repeatedly enduring of harsh sterilization environments. The planar top sheet 40 presents a discrete anterior face surface 42 as its obverse side and an adhering posterior face surface 44 as its reverse side; and is aligned with, is disposed upon, and is permanently adhered in a fluid-tight manner both to the operative, micron-sized, photovoltaic cell-chip transponder unit 40 and the discernible foundation layer 10.

Accordingly, the planar top sheet illustrated by FIG. 8A will have a fixed configuration and millimeter-sized length and width dimensions which are never less than the actual length and width dimensions of the discernible foundation layer - and often are slightly greater in length and width dimensions; and will present a thickness or depth dimension of about 4-6 mills (101.6-152.4 microns) in size—but which optionally can vary from about 3-15 mills in thickness in alternative embodiments, if and when so desired. Accordingly, this discernible foundation layer is longer and extends laterally; but can be cut, however, to any desired size and shape.

₪ The planar top sheet must always provide clear matter or visibly transparent material which allows for both unhindered light energy transmissions and unobstructed responsive RF signal passage on-demand. Thus, the top sheet always will present and include a discernible light energy transmitting zone whose transparent surface area and perimeter edges are aligned with and overlie the photovoltaic cell-chip transponder unit. In each and every embodiment, it is through this definitive light transmitting zone and transparent surface area that light energy signals will travel unhampered and responsive RF signals from the photovoltaic cell-chip transponder unit will freely pass.

In addition, the planar top sheet must always provide clear matter or visibly transparent material through which a person can see the component part number label which might be present at the particular use-tracking badge location. It will be recalled that each of these numbered labels will indicate and state exactly what the corresponding component part number identification is for that specific part. Therefore, the use-tracking badges individually affixed to each of these locations are purposeful overlay variant constructions wherein the planar top sheet of the construct is adequately sized in its length and width dimensions to incorporate and protect the pre-existing part number labels within the overall dimensions of the individual badge as a whole.

B. Properties & Characteristics of the Use-Tracking Badge (i) It is required that each required element in the constructed use-tracking badge as a whole—i.e., the preformed foundation layer, and the photovoltaic cell-chip transponder unit, and the planar top sheet—be firmly attached and permanently joined together in a fluid-tight manner. Such fluid-tight juncture and permanent bonding of essential constituents is necessary to yield a single unified badge composite which: Is protective and safeguarding against external impact forces and collision effects; is repeatedly able to repel water and other aqueous fluids; is highly resistant to cleaning agents and noxious chemical compositions; will repetitiously endure and withstand the extremely harsh treatment conditions of repeated sterilization (via any conventionally known method); and will last for a long-term and indefinite period of usage (extending several calendar years in duration).

The fluid-tight juncture and bonding of these tangible items together preferably employs high-strength, temperature resistant, and long lasting adhesive substances for this purpose. There are today many different conventionally known and commercially available adhesive compounds and bonding compositions that are heat and moisture resistant, that are high temperature durable, and which can effect permanent bonding of multiple discrete layers. All such adhesives and bonding agents are typically applied as a distinct coating to each posterior face surface of each discrete sheet before joining the sheets together in the making of the construct.

(ii). The structural integrity of the constructed three element use-tracking badge will remain resilient, materially uniform and dimensionally unaltered over its entire lifetime of intended and expected usage.

(iii). The construction of the use-tracking badge will adequately protect and long safeguard the embedded photovoltaic cell-activated transponder unit from major impact forces and the damaging effects of inadvertent collisions with other surrounding tangible objects.

(iv). The construction of the use-tracking badge will adequately protect and long safeguard the embedded photovoltaic cell-activated transponder unit from the effects of any stray electrical current(s) which then might be present within the surgical operating room environment.

(iv). The multi-tier use-tracking badge consistently allows light energy photons—i.e., any form, frequency or intensity of light radiation existing either as particles or waves—to pass freely and unhampered through its transparent top planar sheet, and then to enter the embedded photovoltaic cell-activated transponder unit.

(v). The unitary use-tracking badge will on any and all occasions allow radiofrequency (RF) waves and signals generated by the embedded photovoltaic cell-activated transponder unit to travel outwardly; to pass freely through the visibly transparent top planar sheet; and be released into the surrounding air environment.

(vi). The unitary use-tracking badge will typically also include on-demand affixation means—i.e., present a transparent and visibly clear adhesive substance as a discrete coating which lies disposed over the posterior face surface of the foundation layer in the construction; and also provide a peel-away liner joined to the adhesive coating and which is subsequently removed to expose the adhesive for affixation to a pre-chosen location. Thus, given an adhesive substance disposed as a discrete coating upon tile posterior face surface (rearward side) of the foundation layer—the operative use-tracking badge as a whole can become subsequently affixed at will to any chosen surface.

Illustrative Format Variants of & Representative Structural Alternatives for the Use-Tracking Badge

Format Variant A: A Two-Sheet Foundation Layer Construction

The Format Variant A embodiment is illustrated by FIGS. 9A and 9B as a whole, wherein this construction of the use-tracking badge appears in complete and exploded views, in size relationship to a penny sized disc ("PSD"). In this variant instance, the use-tracking badge **50*a*** has particular dimensions which are: A length of about 14 mm, a width of about 5 mm, and a thickness of about 12 mils.

As shown in detail by the exploded view embodiment of FIG. 9A, the discernible foundation layer 10α is formed of two different preformed sheets—a flat backing sheet 12α composed of a dense and visibly colored matter, and a visually-readable numbered label 16α (which presents the component part identification number). The two preformed sheets 12α and 16α are joined together fluid-tight in overlay stacked series; and collectively present a substantially rectangular overall configuration. Also, the two-sheet foundation layer 10α as a whole cumulatively presents an anterior face surface as its obverse side and a posterior face surface as its reverse side. Both the obverse side and the reverse side of the discernible foundation layer **10*a*** have particular functions and applications.

Also as seen in FIG. 9A, an operative, micron-sized, photovoltaic cell-chip transponder unit 30α lies disposed upon and is contained within the anterior face surface area of the two-sheet foundation layer 10α. This photovoltaic cell-chip transponder unit 30α will become activated and energized by light energy; and then will generate and electronically emit an unique RF response signal into the ambient environment, wherein each unique emitted RF signal correlates with and corresponds to a single component part identification number part.

Finally, as shown by FIG. 9A, a preformed, planar top sheet 40α lies disposed upon and is adhered fluid-tight to the photovoltaic cell-chip transponder unit 30α and the anterior face surface of the foundation layer 10α.

The completely erected variant embodiment of the use-tracking badge 50α is illustrated by FIG. 9B. As seen therein, the operative micron-sized photovoltaic cell-integrated chip transponder unit 30α lies embedded within and is completely contained between the planar top sheet 40α and the foundation layer 10α. In this protected position and location, the embedded photovoltaic cell-integrated chip transponder unit 30α can be activated and energized by light energy photons on-demand. Then, after receiving and converting such a light energy transmission, the embedded transponder unit will produce and electronically emit an uniquely encoded RF response signal—which travels through the material thickness of the transparent top planar sheet 40α into the and immediately surrounding environment; and once in the atmosphere of the operating room, can be detected by an adjacently located RF signal receiver, and subsequently then be recorded and stored indefinitely by a RF signal data compilation apparatus.

Format Variant B: A Single Sheet Foundation Layer Construction

The Format Variant B embodiment is illustrated by FIGS. 10A and 10B as a whole; and this use-tracking badge variant 50β appears in complete and exploded views, in size comparison relationship to a penny sized disc ("PSD"). In this variant embodiment, the use-tracking badge 50β has particular dimensions which are: A length of about 14 mm, a width of about 5 mm, and a thickness of about 12 mils.

As shown in detail by the exploded view embodiment of FIG. 10A, the discernible foundation layer 10β is formed using a single material sheet—in this instance, a visually-readable, numbered label 16β which shows the specific component part identification number for the component part. The single numbered label 16β is prepared-in-advance as a material sheet; presents a substantially rectangular overall configuration; has an anterior face surface as its obverse side; and presents a posterior face surface as its reverse side.

Also as seen in FIG. 10A, an operative, micron-sized, photovoltaic cell-chip transponder unit 30β lies disposed upon and contained within the anterior face surface area of the single-sheet foundation layer 10β. This photovoltaic cell-chip transponder unit 30β becomes activated and energized by light energy; and will generate and electronically emit an unique RF response signal into the ambient environment, wherein each unique emitted RF signal correlates with and corresponds to a single component part identification number part.

Lastly, as shown by Fig.10A, a preformed, planar top sheet 40β lies disposed upon and adhered fluid-tight to the photovoltaic cell-chip transponder unit 30β and the anterior face surface of the foundation layer 10β.

The completely formed variant embodiment of the use-tracking badge 50β is illustrated by FIG. 10B. As seen therein, the operative micron-sized photovoltaic cell-integrated chip transponder unit 30β lies embedded within and is completely contained between the planar top sheet 40β and the foundation layer 10β. In this protected position and location, the embedded photovoltaic cell-integrated chip transponder unit 30β can be activated and energized by light energy photons on-demand. Then, after receiving and converting such a light energy transmission, the embedded transponder unit will produce and electronically emit an uniquely encoded RF response signal—which travels through the material thickness of the transparent top planar sheet 40β into the and immediately surrounding environment; and once in the atmosphere of the operating room, can be detected by an adjacently located RF signal receiver, and subsequently then be recorded and stored indefinitely by a RF signal data compilation apparatus.

Format Variant T: An In Situ Generated Foundation Layer Construction

The present invention recognizes and expects that in many surgical implant instances, the modular kit(s) will have a plurality of different pre-existing original numbered labels attached to the exposed face surface of the modular kit, each such original numbered label then lying adjacent to the shaped well(s) where one individual component part is housed. Attention is again directed to Prior Art FIG. 6 hereof, as one representative example where many such original numbered labels appear together in one modular kit.

Accordingly, this alternative Format Variant T embodiment knowingly and intentionally employs any one, or merely a few, or many (if not all) of the pre-existing original part number labels (having visible numbers on their face surfaces) as the requisite foundation layer in the badge construction. In point of fact, these pre-existing original labels having visible part numbers on their face surfaces can properly serve as the necessary material sheet and foundation layer of the embodiment; and in this manner, serve as the tangible stratum by which to generate in-situ a complete and operative use-tracking badge 50γ directly upon the face surface of the modular kit.

It is important to understand and appreciate that this in-situ generated alternative Format Variant T embodiment of the use-tracking badge meaningfully and substantively differs from the Format Variant B embodiment (described above and illustrated by FIGS. 10A and 10B herein) in one critical aspect: The maker of this alternative Format Variant T embodiment of the use-tracking badge does NOT himself prepare or create in advance any numbered label as a material sheet. Instead, the maker merely employs a Precursor Construct T kludge, which is formed of two elements only: a micron-sized photovoltaic cell-integrated chip transponder unit and a planar top sheet. This Precursor Construct T kludge and the intended manner of in-situ badge generation is illustrated by FIG. 11.

As shown by the exploded view of FIG. 11, the Precursor Construct T kludge 60γ is an antecedent article of manufacture and a forerunner product formed by a preformed, planar top sheet 40γ and a single operative, micron-sized, photovoltaic cell-chip transponder unit 30γ. The micron-sized, photovoltaic cell-chip transponder unit 30γ lies disposed upon and is adhered fluid-tight to the posterior face surface of the visibly transparent planar top sheet 40γ; and it is noted that that no other material sheet or tangible stratum is present with the confines of the constructed Precursor Construct T kludge 60γ. In particular, please recognize that there is no foundation layer other material sheet as such within the construction of the Precursor Construct T kludge 60γ.

The alternative Format Variant Tembodiment of the use-tracking badge 50γ is then subsequently generated in-situ directly upon the exposed face surface of the modular kit. This in-situ generated event occurs when the Precursor Construct T kludge 60γ is oriented, aligned, and deposited directly over the pre-existing original part number label 70γ (having visible part numbers on its exposed face surface); and the Precursor Construct T kludge 60γ becomes permanently affixed to the pre-existing original part number label 70γ.

Via this act of in-situ affixation and in this manner, the pre-existing original part number label 70γ (with visible numbers on its face surface) thus becomes the necessary material sheet and the requisite foundation layer of the embodiment. Clearly, the Precursor Construct T kludge acts as a discrete intermediate article and product by which to generate in-situ a complete and operative use-tracking badge 50γ at will—directly, at the exact location on the face surface of the modular kit where the original numbered label appears. Then, and only then, is the true and complete alternative Format Variant T embodiment actually generated in-situ in substantive and operative form.

After the alternative Format Variant T embodiment of the use-tracking badge 50γ has in fact been generated in-situ using the pre-existing original numbered label 70γ, then the embedded photovoltaic cell-chip transponder unit 30γ of this embodiment can become activated and energized by light energy; and will generate and electronically emit an unique RF response signal into the ambient environment, wherein each unique emitted RF signal correlates with and corresponds to a single component part identification number part.

Arrangement Requirement 4: At Least One Discernible Modality Disposition-Accounting Assembly The system and arrangement of the present invention requires the presence and use of at least one discrete modality disposition-accounting assembly; a unitary ensemble which is structurally different and functionally distinct from the use-tracking badges described above.

Typically, it is envisioned and expected that only one operative modality disposition-accounting assembly will appear in the system arrangement of the present invention under most surgical circumstances. However, it will be expressly understood that two, or three, or even more discrete modality assemblies can optionally be usefully employed together in the supervisory arrangement in those surgical situations where the complete implant to be engrafted in-vivo is an especially sophisticated and complex apparatus. Thus, the minimal requirement is that there be at least one modality disposition-accounting assembly within the system arrangement.

In addition, although the requisite modality disposition-accounting assembly can and will be operationally located and tangibly positioned anywhere within the existing spatial confines of the operating room or surgical theatre as such—it is preferred and typical that the modality disposition-accounting assembly be affixed (for the ST's convenience) at one preselected site on the exposed face surface of a sterilizable modular kit (which then contains at least some of the requisite component parts for a complete surgical implant).

The Essential Constituents of the Modality Disposition-Accounting Assembly

As the preferred embodiment illustrated by FIGS. 12A and 12B respectively, the modality disposition-accounting assembly 100 appears as a 10 mm width×28 mm length×12 mils thickness construct which safeguards its internal photovoltaic chip transponder contents from attack and degradation by repeated exposures to a harsh sterilizing environment. Solely for illustration purposes, a penny-sized disc (or "PSD") appears in FIG. 12B for making size comparisons visually.

As shown by FIGS. 12A and 12B, the preferred assembly 100 is a unitary construction which presents an array of three discernible mode disposition subassemblies 110, 120, and 130 respectively. Each of these subassemblies 110, 120, and 130 is spaced apart [about 5 mm distance] in sequential series from the others; and each subassembly 110, 120, and 130 is structured as a modality choice entity formed of the following.

Constituent (α): An optionally present, preformed planar base sheet 140 which is composed of a durable and visibly clear light transparent matter. This optionally present clear base sheet in its preferred embodiments:

- has a set elongated configuration and predetermined millimeter-sized length, width, and thickness dimensions;
- presents a discrete anterior face surface and a discrete posterior face surface;
- is repellent to water and other aqueous fluids;
- is resistant to cleaning agents and other noxious chemical compositions;
- is enduring of and resistant to harsh sterilization environments; and
- has a visibly clear adhesive coating disposed upon its posterior face surface.

Constituent (β): A plurality of preformed and differently colored flat backing sheets 150—shown as flat backing sheets 150*a*,150*b*, 150*c*—which are each spaced apart from one another; are collectively linearly oriented and aligned in as a linear row and are individually permanently positioned in separated sequential series. Each of these flat backing sheets 150 presents a recognizably different and disparate colored material which can be easily visually distinguished by the human eye as alternatively colored materials. Cumulatively and collectively, each of the three differently colored flat backing sheets 150*a*, 150*b*, 150*c* in its preferred embodiments:

- has a pre-selected configuration and thickness dimension;
- presents limited length and width millimeter-sized dimensions;
- has an anterior face surface and a posterior face surface of predetermined surface area;
- is repellent to water and other aqueous fluids;
- is resistant to cleaning agents and other noxious chemical compositions;
- is enduring of harsh sterilization environments; and
- has an adhesive coating disposed upon its posterior face surface.

Constituent (γ): Three individual and discrete micron-sized photovoltaic cell-chip transponder units 160—shown as individual transponder units 160*a*, 160*b*, and 160*c* respectively—are cumulatively and collectively disposed in series upon and contained entirely within the anterior face surface area for each of said three colored intermediate backing sheets 150. In addition, each of said three photovoltaic cell-chip transponder units 140*a*, 140*b*, and 140*c* can be separately activated and individually energized by light energy to generate and electronically emit one corresponding singular and unique identifying RF response signal into the ambient environment.

And

Constituent (δ): A single, preformed planar top sheet 170 which lies disposed upon and joined fluid-tight to each of the three operative micron-sized photovoltaic cell-chip transponder units 160*a*, 160*b*, and 160*c*, as well as to the anterior face surface areas for each of the three colored flat backing sheets 150*a*, 150*b*, and 150*c*.

Accordingly, the planar top sheet 170 in its preferred embodiments:

- is composed entirely of a durable, visibly clear, transparent material;
- presents a discrete anterior face sheet surface and a discrete posterior face sheet surface;
- has an elongated configuration and millimeter-sized length and width dimensions which are not less than the dimension of said colored backing sheets;
- is repellent to water and other aqueous fluids;
- is resistant to cleaning agents and other noxious chemical compositions;
- is enduring of and resistant to harsh sterilization environments; and
- has a visibly clear, light transparent adhesive coating disposed upon its posterior face surface.

Functionally Independent and Distinct Modality Disposition Subassemblies

The preferred embodiment illustrated by FIGS. 12A and 12B respectively is an unitary modality disposition-accounting assembly 100 which has three discernible subassemblies 110, 120, 130, each of which acts independently from the others as one discrete operative subunit. The three subassemblies 110, 120, 130 are individually activated and separately operative on-demand; and each subassembly visually appears as a differently colored subunit to the human eye; and each subassembly is spaced apart a short distance (typically 3-6 mm) from the others. Together, the three subassemblies are oriented and aligned along a single axis as an organized array; and are collectively and cumulatively positioned in sequential sequence series as a linear row of subunits.

Equally important, each modality subassembly 110, 120, 130 independently identifies and individually accounts for one, and only one, particular transaction pattern and performance activity sequence involving a single number identified component part of the complete implant.

Accordingly, the first modality subassembly 110—when activated and energized by light energy photons -will independently release and broadcast a first unique modality RF signal which, in turn, will serve to indicate a first mode of transaction and performance history for that specific component number identified part.

Similarly, if and when the second modality subassembly 120 becomes activated and energized by light energy photons, the subunit 120 will independently release a second modality RF signal which uniquely serves to indicate a different second mode of specific transaction and performance history for that component number identified part.

Lastly, if and when the third modality subassembly 106 is activated and energized by light energy photons, the subunit 130 will then independently release and broadcast a third modality RF signal which provides a third and alterative transaction pattern and performance history for a component number identified part.

Examples of the Different Modes of Surgical Transaction & Performance

In the preferred embodiment shown by FIGS. 12A and 12B respectively, the constructed operational assembly 100 offers and provides a range of not less than three different surgical use patterns as distinct transactions and alternative performance outcomes. It is critical that the substantive differences separating these three surgical transaction patterns and performance histories be properly understood and fully appreciated.

By commonly accepted dictionary definition, the term 'modality' is understood to mean the way or mode in which something exists or is done. Also by common dictionary definition, the term 'disposition' is understood to mean the manner in which something is placed or arranged, especially in relation to other things then also appearing in the same locale.

Therefore as employed herein, the term 'modality disposition' will define the exact nature of one surgical act, activity, and engrafting performance history occurring for a specific number-identified component part which is then being used for a complete implant construct; and this term will identify the true factual outcome and ultimate surgical fate for that single component number-identified part.

Also within the surgical context of the present invention, the term 'accounting' will be understood to be limited to a manner of summarizing individual transactions and performance histories via a unique RF signal which is released and broadcast into the surrounding operating room environment. Accordingly, the accounting function and capability of the 'modality assembly' identifies and summarizes the true transaction history and ultimate outcome of a one transaction or performance activity by the surgeon.

The preferred embodiment of the modality disposition-accounting assembly 100 illustrated by FIGS. 12A and 12B respectively will identify and summarize which of three possible and most-likely transaction patterns and performance outcomes did in fact occur concerning one individual number identified component part as actually used by the surgeon during the in-vivo engrafting procedure. Within the confines of a traditional surgical operating room, the three most likely kinds of surgical transactions and alternative ultimate disposition outcomes are deemed to be these presented below.

Mode of Transaction & Performance History 1

In this $1^{st}$ transaction pattern, the particular component number identified part (such as a 4 mm length, 1 mm diameter, Philips screw) was requested by the surgeon; and was aseptically handed to the surgeon by the ST; and then was successfully surgically placed and inserted into the patient's body at a prechosen anatomic site. In this 1st pattern, the transaction (an insertion of the 4 mm screw into the patient) was surgically successful; and thus the ultimate disposition in this $1^{st}$ pattern instance is that this particular number identified component part (the 4 mm Philips screw) now actually resides and can be found in-vivo at one precisely known location within the body of the living patient.

Accordingly, when the screw was aseptically handed to the surgeon by the ST, the first modality subassembly 110 of the assembly 100 was concurrently activated and energized by light energy photons; and this act in turn released a first unique modality RF signal into the ambient environment. The broadcast of this first unique modality RF signal overtly serves to indicate that a first mode of transaction and performance history for that single component number identified part, the 4 mm Philips screw; and acts to account for a successful insertion of that 4 mm screw as the ultimate disposition and final result as the direct consequence of this transaction.

It will be noted and appreciated also that the operational capabilities of the modality subassembly 110 are limited and restricted to indicating only this first type of transactional and performance history—where the ultimate disposition and result is that the particular component part now actually resides in the living body of the patient.

Mode of Transaction & Performance History 2

In this $2^{nd}$ transaction pattern, the particular component number identified part (such as a 4 mm length, 1 mm diameter, Philips screw) was requested by the surgeon; was aseptically handed to the surgeon by the ST; and was initially placed into the patient's body at a prechosen anatomic site—but was subsequently removed [for any reason] from the subject's body in a re-usable condition. Then, because that part was re-usable, that 4 mm Philips screw was replaced back into its individual shaped well within the modular kit. The outcome and ultimate disposition of this second circumstance is that this particular component part—although initially used by the surgeon—nevertheless was removed and now presently resides again within the modular kit.

To indicate this second fact pattern, the second modality subassembly 120 of the assembly 100 has been activated and energized by light energy photons; and in turn, has independently released a second unique modality RF signal—which serves to identify that this particular 4 mm screw is not actually in the patient. Instead, the broadcast of thee second modality RF signal will act to account for the actual return of the 4 mm screw to the modular kit as the ultimate disposition and performance outcome for that screw as the direct consequence of this transaction.

It will be notcd and appreciated, aydin, that the operational capabilities of the modality subassembly 120 are limited and restricted to indicating only this second type of transactional and performance history—where the ultimate disposition and result is that the particular component part (the 4 mm screw) now resides once again within the modular kit.

Mode of Transaction & Performance History 3

In this $3^{rd}$ transaction pattern , the particular component number identified part (such as a 4 mm length, 1 mm diameter, Philips screw) was requested by the surgeon; was aseptically handed to the surgeon by the ST; was initially inserted into the patient's body—but was subsequently removed from the patient (for any given reason) in a non-usable condition. Furthermore, because this component number identified part (the 4 mm Philips screw) was bent or modified by the surgeon, or was defective in its performance, or was deficient in its requisite screw thread properties—that particular Philips 4 mm screw was then discarded by the surgeon as waste matter, and was removed from the surgical field, and eliminated forever from any further possible surgical use. Accordingly, the outcome and ultimate disposition of this third surgical transaction pattern is that this particular component part (the 4 mm Philips screw) lies neither within the patient's body, nor has it been returned to the modular kit inventory; but instead has been removed from use entirely, and has been knowingly discarded as surgical trash.

In this alternative third performance pattern, the third modality subassembly 130 of the badge assembly 100 has been activated and energized by light energy photons; and has independently released a third unique modality RF signal which will serve to identify that the component number identified part (the 4 mm screw) is not in the patient, and has not been returned to the modular kit inventory—but instead has been discarded as surgical waste mater.

Once again, it is understood that that the operational capabilities of the modality subassembly 130 are limited and restricted to indicating only this third pattern type of transactional and performance history—where the ultimate disposition and result is that the 4mm screw is now mere medical trash.

The Scope of the Envisioned Variants (a). There are always a plurality of discernible modality disposition sub-assembly units in the erected assembly, each discrete section and subunit being spaced apart from the others in sequential series. These multiple subunits cumulatively and collectively appear as an array of aligned individually operative subassemblies, which are oriented and positioned in a linear row across the length dimension of the erected assembly as a whole, as seen in FIG. 12B. Accordingly, in each and every embodiment of the modality disposition-accounting assembly, there will be not less than two (2) and not more than six (6) discrete subassembly sections spaced apart a few millimeters distance from one another.

(b). A preformed planar base sheet 140 (seen in FIG. 12A) is desirably, but optionally, present in any given embodiment of the modality disposition-accounting assembly. When present, this base sheet is composed of a durable and visibly clear light transparent matter; and all the other required constituents of the assembly as a whole are then located and held in desired positioned upon the anterior face surface of the clear base sheet.

(c). If and when the preformed planar base sheet is not present as such in the particular embodiment, then this variant format appears and is constructed as illustrated by FIG. 13. A plurality of preformed and differently colored flat backing sheets 150—shown as flat backing sheets 150*i*,15*ii*, 150*iii*—which are each spaced apart from one another; are collectively linearly oriented and aligned in as a linear row and are individually permanently positioned in separated sequential series. Each of these flat backing sheets 150 presents a recognizably different and disparate colored material which can be easily visually distinguished by the human eye as alternatively colored materials. Also, three individual and discrete micron-sized photovoltaic cell-chip transponder units 160*i*, 160*ii*, and 160*iii* respectively are cumulatively and collectively disposed in series upon and contained entirely within the anterior face surface area for each of said three colored intermediate backing sheets 150. Finally, a single, preformed planar top sheet 170*i* lies disposed upon and joined fluid-tight to each of the three operative micron-sized photovoltaic cell-chip transponder units 160*i*, 160*ii*, and 160*iii*, as well as to the anterior face surface areas for each of the three colored flat backing sheets 150*i*, 150*ii*, and 150*iii*.

(d). The true number of preformed and differently colored backing sheets and the number of micron-sized photovoltaic cell-chip transponder units in each constructed embodiment of the modality disposition-accounting assembly will vary directly and correspond exactly with the desired number of individual subassembly units. Thus, if the minimal two modality subassemblies are to be arrayed in the embodiment, then only two differently colored flat backing sheets and only two micron-sized photovoltaic cell-chip transponder units will be concomitantly present in this particular embodiment. Similarly, if the maximum six modality subassemblies are to appear in the given embodiment, then six differently colored flat backing sheets and six discrete micron-sized photovoltaic cell-chip transponder units will be present in this alternative embodiment.

(e). For each modality disposition subassembly present in the assembly as a whole, each such subassembly will display a recognizably different and disparate colored material which can be easily visually distinguished by the human eye as alternatively colored materials. It is recommended and preferred that the different colors chosen for use will be vivid shades and bold hues such that there will be little or no difficulty in distinguishing among the range and variety of colors as separated operational subassembly segments.

(f). Because the disposition-accounting function and capability of each modality disposition subassembly appearing within the assembly as a whole must identify and summarize one, and only one, surgical transaction pattern and ultimate outcome for a single component number identified part as actually used by the surgeon—it is vital that the particular embodiment be prepared and erected to provide a sufficient number of possible surgical transaction patterns and ultimate performance outcomes that are realistically consistent with the kind and type of complete implant construct which is being engrafted in-vivo. Accordingly, it will be understood that a first type of complete implant construct, such as an "implantable defibrillator", will present the need for a greater number of possible alternative transaction patterns—and for more modality subassembly units than will an "internal fixator" such as a single bone plate.

Arrangement Requirement 5: A Light-Energy Emitting Wand

For purposes of the present invention, a light-emitting wand is defined as any small, hand-holdable baton, stick, staff, bar, or dowel-like apparatus which can generate a stream of photons on-demand; has a fixed beam diameter size; and will emit light energy photons at a prechosen light wavelength and at a pre-determined light intensity.

Such light-emitting devices have been known conventionally for many years; and one generally useful prior art example is described by U.S. Pat. No. 6,293,684 [of E. L. Riblett issued on Sep. 25, 2001]. As disclosed therein, the wand light has a base tube with a light-tube end in which a base end of a light tube is pivotal concentrically with pivotal-light-switch attachment of the light tube to the base tube. The base tube contains a stored-energy unit, in addition to being a handle and a daytime signaler. The light tube contains a light emitter which can include a flashlight bulb or a plurality of light-emitting diode units on a circuit board. The light tube is twisted in the base tube for selective switching of current for the light emitter.

Quite often, a wand light will comprise a laser diode, a programmable current driver, and an optical collimation/focusing module. Many styles of light-emitting wands are known and conventionally available today for a variety of purposes; and a wide range of operative models are sold commercially. Thus, for the present invention in many of its preferred embodiments, the wand will comprise an operative laser apparatus—which, for example, can emit an average of 60 mW of optical power at a frequency of 658 nm; and be pulsed at 1 MHz.

The preferred, tightly focused, narrow light beam emitted by the laser diode of the wand also offers some unique benefits: It allows for precise positional specificity that can be applied to small and closely spaced items. This desirable capability allows the human user the capability of physically to address and to illuminate one micron-sized photovoltaic cell-chip transponder unit at a time -despite that these a plurality of such transponder unit lie together in close proximity to each as a dense array of micron-sized photovoltaic cell-chip transponder units. In this manner, only one specific photovoltaic cell-chip transponder unit is energized at a time; and only one response RF signal at a time is subsequently released by the energized transponder unit into the ambient environment.

It will be noted and appreciated that this particular feature and capability is not feasible with conventional RFID tags and methods because an array of RFID tags disposed in close proximity will attempt to communicate simultaneously, and will mutually interfere with one another; and thus preclude and prevent individual activation of the tags—a phenomenon known as "RFID tag collision".

A Preferred Wand Embodiment

A preferred embodiment of the light-emitting wand is commercially sold by PharmaSeq Wand; and is a small, hand-held device capable of energizing and then receiving the RF response signal released by individual micron-sized photovoltaic cell-chip transponders, one at a time. Such a preferred wand 200 is about 17.5 cm in length; is about 2.8 cm in diameter; and appears as FIG. 14.

As seen therein, the wand 200 is electronically connected to a conventional personal computer or laptop via a USB cable that provides both electrical power and direct electronic communication. Typically, the wand 200 can be either hand-held or be mounted on a fixed stand.

The wand 200 generally comprises: a laser diode with programmable laser driver, an optical focusing module, an air coil pickup connected to an RF receiver, a USB 2.0 microcontroller and power regulators. The laser typically emits 5 to 60 mW of optical power at 660 nm; and is registered with the FDA as a Class 3R device, similar to a laser pointer.

Operationally when placed over a micron-sized photovoltaic cell-chip transponder, the light photons emitted by the wand causes the transponder unit to become activated and energized; and to generate and broadcast a uniquely encoded RF response signal into the surrounding ambient environment.

Arrangement Requirement 6: A Discernible Telemetric RF Signal Receiver

By definition, an RF signal receiver is any telemetric electronic device able to receive a range of different and diverse RF response signals as they individually are released and broadcast into the ambient environment. In turn, telemetry is defined as the sensing and measuring of information at some remote location and then transmitting that information to a different central or host location; and once there, the transferred signal information can be recorded, compiled, analyzed, and used to control a process.

Telemetry RF signal receivers are well known and conventionally used articles of manufacture [see for example, Telemetry Standard RCC Document 106-07, Chapter 2, September 2007]; and are thus discrete acquisition units of individual RF signals which have been broadcast into the environment. As such, RF signal receivers are electronic units operative to receive RF signal transmissions from remote locations via wireless communication; and then are able subsequently to transfer them electronically to another apparatus for recording, compilation, analysis, and visualization of information.

The RF signal receiver units suitable for use in the present invention will each exhibit and collectively share several operating parameters and performance characteristics, which include the following:

- An operating frequency, which is the full range of specific RF signals that can be received;
- A measurement resolution, which is the minimum digital resolution possible for that unit;
- A maximum transmission distance, which is the greatest measurable distance that the receiver unit can be physically separated from the transponder source of the RF signal and still be able to receive that transmitted RF signal;
- A fixed data rate, which is the amount of RF signal data in bits per second that can be transferred subsequently by the receiver unit; and
- A rated output power, which is the maximum signal communication power that the receiver unit can transmit and transfer its received signal data to another electronic device.

Consequently, the RF signal receiver unit is telemetric device that is typically connected to and is in electronic communication with a remotely located standard PC unit; and often appears today as a USB-powered unit containing a USB 2.0 transceiver microcontroller, a field programmable gate array code (FPGA), some power converters and regulators, and a tuned air coil pickup with a high gain. Most desirably, it is a low noise differential RF signal receiver with hysteretic comparator data slicer; and the FPGA code can be periodically upgraded to support incorporation of new features and performance enhancements.

A Preferred Format

It is most desirable that the RF signal reader 300 be located at the distal end of the wand 200, as has been described above and as shown by FIG. 14. In this distal location setting, the RF signal reader 300 is capable of receiving the RF response signal and reading the encoded component part identification number broadcast by the individual photovoltaic transponders.

A portable wand combined with a RF signal ID reader is commercially available from the manufacturer [Pharmaseq Inc., Princeton N.J.]; and such an remotely located response-signal ID reader/detector can and will communicate with any personal computer (PC) system via a standard USB port. Thus, the Series 8000 PharmaSeq Wand is both suitable and operative for detecting and reading responsive RF signals sent from embedded P-Chip® transponders. This response-signal ID reader/detector is calibrated for object identification applications; and includes CD-ROM with p-Chip Reader Software (compatible with Microsoft Excel, Access, and similar software programs).

Accordingly as seen in FIG. 14, the RF signal reader 300 is located at the distal end of the wand 200; and is a USB-powered device typically connected to a standard PC. It often includes a USB 2.0 microcontroller, field programmable gate array, power regulators, and a radiofrequency receiver-coil assembly. It instantly receives and decodes the broadcast RF response signal; determines the identity information from the received RF signal using internal onboard firmware; and then reports the decoded identity information to a nearby data compilation unit via programmed software. The RF signal identity information is decoded and transmitted in a matter of milliseconds; and thus a minimum of time is required for the data to be recorded and visualized.

Internal software processes the received RF response signals using an error checking decode algorithm; and transmits them, along with a log of activities, in an MS SQL database or other type of file specified by the user. The available software includes DLL and LabView application programming interfaces. Exporting data directly to MS Excel programming is also an option.

Arrangement Requirement 7: At Least One RF Signal Recordation and Data Compilation Unit In the present system, a RF signal recordation and data compilation unit is in operative electronic communication with the RF signal receiver described above. This RF signal recordation and data compilation unit provides a range of desired functions and capabilities: It accumulates, records and stores all received RF response signals as informational data; compiles and analyzes the stored RF informational data; and can display the complied and analyzed RF informational data in at least one visual display format.

Many suitable RF signal compilation units are known in the relevant prior art and have been conventionally employed over several decades. Accordingly, for these reasons, for achieving the goals and purposes of the present invention—any kind, type, format, or style of conventional RF signal recordation and compilation unit is suitable and acceptable, so long as the necessary functions and essential actions of recording and storing all received RF response signals as informational data is performed.

Thus, once all the broadcasted RF signal responses have been entered and recorded as stored data, the surgical technologist can then employ a wide range of different software programs to perform a host of additional functions—such as compiling and analyzing the stored RF informational data, as well as displaying the complied and analyzed RF informational data in a desired visual presentation format.

IV. The Methodology of the Control System & Supervisory Arrangement

It is most desirable that no doubt or question remain or exist as to how to use the present invention in its intended surgical setting. For this reason, a summary description of the manner in which the present control system and supervisory arrangement would be operative and be used within the limited spatial confines of an Operating Room is given below.

"Build a Patient Case History"

Initially, the true numbered identities and individual component part contents of one or more modular kits, trays, or surgical sets which are needed and used for the engrafting of a complete implant are scanned into a software management program—as a group of items specific to the particular patient case. This is typically done before the surgery actually begins; and will routinely occur when the requisite tangible supplies and disposables to be used in the patient's surgery are put on a cart specific to that surgery (i.e., a patient's "case cart").

When these items are scanned and associated as a group, the user will assign a surgeon's name, a patient case time, and a surgical implant procedure title from a prepared menu offered by the software. The modular kits, trays, or sets are then set up for the operation, usually on the patient's case cart for that particular surgery.

This preliminary action and activity is performed outside the Operating Room itself, usually in Central Supply or in the Sterile Processing Department. The prepared-in-advance cart is then moved and staged outside the OR until it is needed for the particular surgery.

"Scan the Implant Parts"

Three people will typically interact with the control system in the operating room itself. These are: The surgeon(s), the surgical technician ("ST"), and the circulating nurse.

The circulating nurse is the person responsible for all surgeon support activities outside the sterile field during the surgery. In comparison, the surgical technician (or ST) is the person responsible for surgeon assistance and support within the sterile field (outside of anesthesia). The ST organizes and hands off the various tools and instruments, requisite implant component parts, and necessary medical supplies to the surgeon during the course and performance of the surgery—when and as requested by the surgeon.

Once the surgery is underway, the surgeon will call for each of the implant parts he is to engraft into the patient. The previously-prepared patient's case cart will be drawn close by the circulating nurse to the sterile operating field and anatomic site; and the circulating nurse then typically stands across from the ST at the other side of the patient. The patient's case cart will remain a short distance [typically a distance of about 1 foot] from the patient so as to not contaminate the sterile operating field.

Typically at this point, the surgical technician will then open the sterile packaging containing the preferred wand embodiment—a combination laser light and telemetric RF reader (described in particular detail above)—within the confines of the sterile field; the packaged wand having been previously sterilized via a chemical sterilization process (such as Sterad). The surgical technician then typically "hands off" the USB end of the connecting cord of the wand to the circulating nurse (who is not in sterile garb and thus stands outside of the sterile operating field).

The circulating nurse will then plug the USB end of the wand cord into a separately prepared data-cart which contains and provides at least one RF data compilation unit; and preferably is a wireless and battery powered article suitable for electronic communication. Once the connections are complete, the circulating nurse then engages the software programs of the RF data compilation unit into the "scan implants" mode via the data-cart touch screen.

At this stage, the ST can then begin to select and to hand the individual component parts called for by the surgeon as requested. The software of the RF data compilation unit automatically defaults when started into the "implanted into patient" mode of transaction and performance; and each time the ST selects and hands the surgeon an engraftable part, the ST will scan the corresponding use-tracking badge correlating to that specifically numbered component part then disposed upon the exposed face surface of the modular kit or tray; and via this act, the particular information will become automatically entered into and retained by the electronic memory of the RF data compilation unit on the data-cart.

If at any time, should the ST be given a specific component part back by the surgeon which is deemed to be intact, can be used again, and thus can be returned back into the modular kit or tray—the ST will then light energy scan the particular subassembly unit of the modular assembly which designates this activity as a "removal and return of the part back into the modular kit inventory"; and then also light scan the corresponding use-tracking badge on the modular kit or tray which corresponds to and correlates with that one particular component part. By these actions, the control system records the details of the event whereby that component part is return to its previous place within the modular kit.

In the alternative instance, if and when the component part is handed back to the ST by the surgeon because it then is insufficient in quality, or is somehow defective, or is deemed to be unsuitable for any reason; then, the ST would light energy scan the alternative performance modular subassembly unit. This particular act by the ST indicates that the specific component part is truly unfit and unsuitable for any use. The ST will then also light scan the proper corresponding use-tracking badge disposed on the exposed face surface of the modular kit or tray which corresponds to and correlates with that particular component part—which is now identified as being mere surgical waste.

"After the Surgery is Completed"

At the end of the engrafting surgery as a whole, the circulating nurse pushes the "save" and "print" buttons appearing on the screen of the RF data compilation unit then resting on the data-cart. The operative supervisory arrangement and control system will then save all the data previously entered which is pertinent to the patient's surgery and case history; and pass that recorded information to other software systems—in particular, to the inventory management and patient billing/patient record software, as well as to the software drivers to create a written printout of all the tangible items and supplies actually used for that particular surgery.

It should be noted here also that—both for convenience and accommodation—one part of the RF data compilation unit on the data-cart desirably includes and provides a standard barcode scanner; i.e., a scanner which can be used to scan and track by conventional barcodes all pre-sterile supplies (e.g., gloves, suture, saline, biomaterials, biologics, etc.) that are put into the sterile operating field for use during the surgery. These commonplace items all are presently available in closed packaging which after sterilization keeps them sterile indefinitely; and such items typically have pre-printed barcode identification labels on their exterior package surfaces. In this manner, all currently used surgical items which are today traditionally identified by barcode labels can be used conveniently with the control system and supervisory arrangement of the present invention.

The present invention is neither limited in form nor restricted in scope except by the claims appended hereto.

What we claim is:

1. A parts-inventory control system for tracking the use of and accounting for the ultimate disposition of at least some of the component parts needed for engrafting a complete implant as each individual component part is separately surgically introduced in-vivo at a preselected anatomic site upon or within the body of a living subject, said parts-inventory control system comprising:

(1) a prepared-in-advance, inventory-parts dual correlation whereby a $1^{st}$ correlation links each component part of the complete implant with a corresponding component part identification number, and wherein the $2^{nd}$ correlation links each of said component part identification numbers with a corresponding singular RF signal;

(2) a preformed, sterilizable on-demand, modular kit housing at least some of the component parts needed for engrafting a complete implant which is to be surgically introduced in-vivo upon or within the body of a living subject, wherein said modular kit has set dimensions, a fixed configuration, a discernible face surface, and a plurality of shaped wells suitable for individually housing said component parts;

(3) a plurality of discrete use-tracking badges individually suitable for affixation at a pre-selected location on a face surface of said modular kit, wherein each of said use-tracking badges corresponds to a unique component part identification number and is able to release a corresponding singular RF signal on-demand into the ambient environment, and wherein each of said use-tracking badges is comprised of (α) a discernible foundation layer having set dimensions, a fixed configuration, and an exposed face surface, said foundation layer being formed of at least one and not more than three different preformed sheets joined together in overlay series, each of said preformed sheet being selected from the group consisting of a flat backing sheet composed of a dense and visibly colored matter, a planar sheet composed of durable and visibly clear light transparent material, and a numbered label indicative of one specific component part of said complete implant, (β) an operative, micron-sized, photovoltaic cell-chip transponder unit disposed upon and contained within the surface area of said foundation layer, said photovoltaic cell-chip transponder unit becoming activated and energized by light energy to generate and electronically emit a singular RF response signal indicative of a specific component part number into the ambient environment, and (γ) a preformed planar top sheet disposed upon and adhered fluid-tight to said photovoltaic cell-chip transponder unit and the face surface of said foundation layer;

(4) at least one discernible modality disposition-accounting assembly suitable for on-demand affixation at a preselected location within the spatial confines of the operating room, wherein said modality disposition-accounting assembly presents an array of not less than two and not more than six transaction mode subassembly units and wherein each of said subassembly units in said array is spaced apart from the others in sequential series, said modality disposition-accounting assembly comprising (α) an optionally present, preformed planar base sheet composed of a durable and visibly clear light transparent matter, wherein said optionally present planar base sheet has a set elongated configuration and predetermined millimeter-sized length, width, and thickness dimensions, presents a discrete anterior face surface and a discrete posterior face surface, and has a visibly clear adhesive coating disposed upon its posterior face surface, (β) a plurality of preformed flat backing sheets which are each oriented and aligned, spaced apart, and positioned in sequential series, wherein each of said preformed flat backing sheets is composed of a recognizably different and visually distinguishable colored material, and wherein each of said colored preformed flat backing sheets has a preselected configuration and thickness dimension, presents limited length and width millimeter-sized dimensions, and has an anterior face surface and a posterior face surface of predetermined surface area, (γ) one discrete operative micron-sized photovoltaic cell-chip transponder units disposed upon and contained entirely within the anterior face surface area for each of said colored backing sheets, wherein each of said photovoltaic cell-chip transponder units is separately activated and individually energized by light energy to generate and electronically emit one singular RF response signal into the ambient environment, and (δ) a preformed planar top sheet disposed upon and joined fluid-tight to each of said operative micron-sized photovoltaic cell-chip transponder units and to said anterior face surface area of each of said colored backing sheets, wherein said planar top sheet is composed entirely of a durable, visibly clear, transparent material, presents a discrete anterior face sheet surface and a discrete posterior face sheet surface, has an elongated configuration and millimeter-sized length and width dimensions which are not less than the dimension of said colored backing sheets, has a visibly clear, light transparent adhesive coating disposed upon its posterior face surface;

(5) a preformed, light-energy emitting on-demand, wand which generates a photon stream, has a fixed light beam diameter size, and emits light at a prechosen wavelength and at a pre-determined intensity;

(6) a telemetric RF signal receiver able to receive and then convey a range of different and diverse RF response signals after said RF signals are generated and released into the ambient environment; and (7) at least one RF signal compilation unit in communication with said RF signal receiver, wherein said RF signal compilation unit accepts, accumulates and records all conveyed RF response signals as data, compiles and analyzes the conveyed RF signal data, and is able to display the conveyed RF signal data in at least one visual format.

2. The parts-inventory control system as recited by claim 1 wherein each of said use-tracking badges is a millimeter-sized article of manufacture which safeguards its photovoltaic cell-chip transponder unit from degradation by a harsh sterilizing environment.

3. The parts-inventory control system as recited by claim 1 wherein the surgical implant being engrafted in-vivo is one selected from the group consisting of prostheses, drug delivery devices, sensor articles, fixation hardware, and repair structures.

4. The parts-inventory control system as recited by claim 1 wherein the surgical implant being engrafted in-vivo is one selected from the group consisting of sensory devices, neurological items, cardiovascular devices, orthopedic structures, contraceptives, and cosmetics.

5. The parts-inventory control system as recited by claim 1 wherein said modular kit houses at least some of the hardware component parts required by the surgical implant being engrafted in-vivo.

* * * * *